US012207908B2

(12) United States Patent
Vajdic et al.

(10) Patent No.: US 12,207,908 B2
(45) Date of Patent: Jan. 28, 2025

(54) COMPACT MOBILE THREE-LEAD CARDIAC MONITORING DEVICE

(71) Applicant: HEARTBEAM, INC., Santa Clara, CA (US)

(72) Inventors: Branislav Vajdic, Los Gatos, CA (US); Bosko Vulicevic, Belgrade (RS); Ljupco Hadzievski, Belgrade (RS)

(73) Assignee: HeartBeam, Inc., Santa Clara, CA (US)

( * ) Notice: Subject to any disclaimer, the term of this patent is extended or adjusted under 35 U.S.C. 154(b) by 413 days.

(21) Appl. No.: 17/609,014

(22) PCT Filed: May 13, 2020

(86) PCT No.: PCT/US2020/032556
§ 371 (c)(1),
(2) Date: Nov. 5, 2021

(87) PCT Pub. No.: WO2020/232040
PCT Pub. Date: Nov. 19, 2020

(65) Prior Publication Data
US 2022/0211287 A1     Jul. 7, 2022

Related U.S. Application Data

(60) Provisional application No. 62/847,308, filed on May 13, 2019.

(51) Int. Cl.
*A61B 5/282* (2021.01)
*A61B 5/00* (2006.01)
(Continued)

(52) U.S. Cl.
CPC ........ *A61B 5/02438* (2013.01); *A61B 5/0006* (2013.01); *A61B 5/0022* (2013.01);
(Continued)

(58) Field of Classification Search
CPC ... A61B 5/02438; A61B 5/0006; A61B 5/282; A61B 2560/04
See application file for complete search history.

(56) References Cited

U.S. PATENT DOCUMENTS 4,216,780 A   8/1980 Rubel
4,850,370 A   7/1989 Dower
(Continued)

FOREIGN PATENT DOCUMENTS

CN   1668242 A   9/2005
CN   1870937 A   11/2006
(Continued)

OTHER PUBLICATIONS

Vajdic et al.; U.S. Appl. No. 18/260,318 entitled "Anbulatory electrocardiogram patch devices and methods," filed Jul. 3, 2023.
(Continued)

*Primary Examiner* — Lynsey C Eiseman
*Assistant Examiner* — James Moss
(74) *Attorney, Agent, or Firm* — Shay Glenn LLP

(57) ABSTRACT

Compact, mobile three-lead cardiac monitoring devices for remote detection and/or diagnosis of cardiac events (e.g., acute myocardial infarction). The apparatus may include two integrated hand electrodes and two chest electrodes disposed on two pivotable arms that are capable of retracting in the compartments, enabling a compact size when the device is not used. Also described herein are systems including these devices and methods of using them.

18 Claims, 10 Drawing Sheets

(51) Int. Cl.
- *A61B 5/024* (2006.01)
- *A61B 5/26* (2021.01)
- *A61B 5/346* (2021.01)
- *G16H 50/30* (2018.01)

(52) U.S. Cl.
CPC ............. *A61B 5/0024* (2013.01); *A61B 5/26* (2021.01); *A61B 5/282* (2021.01); *A61B 5/346* (2021.01); *A61B 5/6823* (2013.01); *A61B 5/6826* (2013.01); *A61B 5/74* (2013.01); *G16H 50/30* (2018.01); *A61B 2560/04* (2013.01)

(56) References Cited

U.S. PATENT DOCUMENTS

| | | | |
|---|---|---|---|
| 5,339,823 A * | 8/1994 | Reinhold, Jr. | A61B 5/282 600/509 |
| 5,630,664 A | 5/1997 | Farrelly | |
| 5,724,580 A | 3/1998 | Levin et al. | |
| 6,047,203 A | 4/2000 | Sackner et al. | |
| 6,052,615 A | 4/2000 | Feild et al. | |
| 6,363,274 B1 | 3/2002 | Scalisi et al. | |
| 6,507,753 B1 | 1/2003 | Xue et al. | |
| 6,607,480 B1 | 8/2003 | Bousseljot et al. | |
| 6,625,483 B2 | 9/2003 | Hoium et al. | |
| 7,266,408 B2 | 9/2007 | Bojovic et al. | |
| 7,477,935 B2 | 1/2009 | Palreddy et al. | |
| 7,647,093 B2 | 1/2010 | Bojovic et al. | |
| 7,801,591 B1 | 9/2010 | Shusterman | |
| 8,209,002 B2 | 6/2012 | Vajdic et al. | |
| 8,369,936 B2 | 2/2013 | Farringdon et al. | |
| 8,615,290 B2 | 12/2013 | Lin et al. | |
| 8,676,304 B2 | 3/2014 | Fischell et al. | |
| 8,700,137 B2 | 4/2014 | Albert | |
| 8,781,566 B2 | 7/2014 | John et al. | |
| 8,818,482 B2 | 8/2014 | Phillips et al. | |
| 9,005,129 B2 | 4/2015 | Venkatraman et al. | |
| 9,364,158 B2 | 6/2016 | Banet et al. | |
| 9,980,678 B2 | 5/2018 | Chan et al. | |
| 10,117,592 B2 | 11/2018 | Bojovic et al. | |
| 10,154,460 B1 | 12/2018 | Miller et al. | |
| 10,433,744 B2 | 10/2019 | Bojovic et al. | |
| 10,499,850 B2 | 12/2019 | Fuerst et al. | |
| 10,709,339 B1 | 7/2020 | Lusted | |
| 10,729,347 B1 | 8/2020 | Schleicher | |
| 11,071,490 B1 | 7/2021 | Vajdic et al. | |
| 11,234,658 B2 | 2/2022 | Persen et al. | |
| 11,412,972 B2 | 8/2022 | Persen et al. | |
| 2002/0045836 A1 | 4/2002 | Alkawwas | |
| 2003/0032871 A1 | 2/2003 | Selker et al. | |
| 2003/0083586 A1 | 5/2003 | Ferek-Petric | |
| 2003/0083587 A1 | 5/2003 | Ferek-Petric | |
| 2004/0015091 A1 | 1/2004 | Greenwald et al. | |
| 2004/0087864 A1 | 5/2004 | Grouse | |
| 2004/0092836 A1 | 5/2004 | Ritscher et al. | |
| 2004/0138574 A1 | 7/2004 | Groenewegen et al. | |
| 2005/0027203 A1 | 2/2005 | Umeda et al. | |
| 2005/0049663 A1 | 3/2005 | Harris et al. | |
| 2005/0215918 A1 | 9/2005 | Frantz et al. | |
| 2005/0234354 A1 | 10/2005 | Rowlandson et al. | |
| 2006/0009698 A1 | 1/2006 | Banet et al. | |
| 2006/0030782 A1 | 2/2006 | Shennib | |
| 2006/0224072 A1 | 10/2006 | Shennib | |
| 2006/0244465 A1 | 11/2006 | Kroh et al. | |
| 2007/0021677 A1 | 1/2007 | Markel | |
| 2007/0100666 A1 | 5/2007 | Stivoric et al. | |
| 2008/0027330 A1 | 1/2008 | Naghavi et al. | |
| 2008/0113650 A1 | 5/2008 | Engstrom | |
| 2008/0161715 A1 | 7/2008 | Stivoric et al. | |
| 2008/0281180 A1 | 11/2008 | Choe | |
| 2009/0112105 A1 | 4/2009 | Clayman | |
| 2009/0281421 A1 | 11/2009 | Culp et al. | |
| 2009/0281440 A1 | 11/2009 | Farazi et al. | |
| 2009/0299206 A1 | 12/2009 | Wang et al. | |
| 2010/0017420 A1 | 1/2010 | Archer et al. | |
| 2010/0023081 A1 | 1/2010 | Audet et al. | |
| 2010/0042008 A1 | 2/2010 | Amital et al. | |
| 2010/0076331 A1 | 3/2010 | Chan et al. | |
| 2010/0130845 A1 | 5/2010 | Clayman | |
| 2010/0168593 A1 * | 7/2010 | Sakoda | A61B 5/26 600/509 |
| 2010/0174204 A1 * | 7/2010 | Danteny | A61B 5/411 600/509 |
| 2010/0240980 A1 | 9/2010 | Zhu et al. | |
| 2011/0015496 A1 | 1/2011 | Sherman et al. | |
| 2011/0105928 A1 | 5/2011 | Bojovic et al. | |
| 2011/0124979 A1 | 5/2011 | Heneghan et al. | |
| 2011/0224565 A1 | 9/2011 | Ong et al. | |
| 2011/0237922 A1 | 9/2011 | Parker, III et al. | |
| 2011/0301435 A1 | 12/2011 | Albert et al. | |
| 2011/0306859 A1 | 12/2011 | Saldivar et al. | |
| 2012/0022385 A1 | 1/2012 | Shimuta et al. | |
| 2012/0059271 A1 | 3/2012 | Amital et al. | |
| 2012/0116176 A1 | 5/2012 | Moravec et al. | |
| 2012/0116240 A1 | 5/2012 | Chou | |
| 2012/0136266 A1 | 5/2012 | Grady | |
| 2012/0184858 A1 | 7/2012 | Harlev et al. | |
| 2012/0283586 A1 | 11/2012 | Song et al. | |
| 2013/0125906 A1 | 5/2013 | Hon | |
| 2013/0172723 A1 | 7/2013 | Baxi et al. | |
| 2013/0331665 A1 | 12/2013 | Libbus et al. | |
| 2014/0086346 A1 | 3/2014 | Mottaiyan et al. | |
| 2014/0114166 A1 | 4/2014 | Baxi | |
| 2014/0155723 A1 | 6/2014 | Levin et al. | |
| 2014/0163349 A1 | 6/2014 | Amital et al. | |
| 2014/0221845 A1 | 8/2014 | Mestha et al. | |
| 2014/0257122 A1 | 9/2014 | Ong et al. | |
| 2015/0018660 A1 | 1/2015 | Thomson et al. | |
| 2015/0018693 A1 | 1/2015 | Mestha et al. | |
| 2015/0057512 A1 | 2/2015 | Kapoor | |
| 2015/0119780 A1 | 4/2015 | DeLuke et al. | |
| 2015/0351646 A1 | 12/2015 | Cervini | |
| 2016/0015286 A1 | 1/2016 | Gitlin et al. | |
| 2016/0022162 A1 | 1/2016 | Ong et al. | |
| 2016/0045166 A1 | 2/2016 | Gheeraert et al. | |
| 2016/0113541 A1 | 4/2016 | Hadley et al. | |
| 2016/0135706 A1 | 5/2016 | Sullivan et al. | |
| 2016/0188823 A1 | 6/2016 | Rowlandson et al. | |
| 2016/0287172 A1 | 10/2016 | Morris et al. | |
| 2016/0302677 A1 | 10/2016 | He | |
| 2016/0361023 A1 | 12/2016 | Martin et al. | |
| 2017/0105682 A1 | 4/2017 | MacDonald et al. | |
| 2017/0127966 A1 | 5/2017 | Wu et al. | |
| 2017/0188861 A1 | 7/2017 | Schreck et al. | |
| 2017/0258342 A1 | 9/2017 | Ukil et al. | |
| 2017/0319082 A1 | 11/2017 | Sayme | |
| 2017/0332942 A1 | 11/2017 | Pflugh et al. | |
| 2017/0340218 A1 | 11/2017 | Kuchler et al. | |
| 2018/0004904 A1 | 1/2018 | Phillips | |
| 2018/0043134 A1 | 2/2018 | Alvarez et al. | |
| 2018/0064356 A1 | 3/2018 | Mendenhall et al. | |
| 2018/0116607 A1 | 5/2018 | Yu et al. | |
| 2018/0125385 A1 | 5/2018 | Chauhan et al. | |
| 2018/0199824 A1 | 7/2018 | Centen et al. | |
| 2018/0316781 A1 | 11/2018 | Salem | |
| 2018/0336969 A1 | 11/2018 | Jabourian | |
| 2019/0069789 A1 | 3/2019 | Bojovic et al. | |
| 2019/0117100 A1 | 4/2019 | Rollie et al. | |
| 2019/0290147 A1 | 9/2019 | Persen et al. | |
| 2019/0298200 A1 | 10/2019 | Wiesel | |
| 2019/0298209 A1 | 10/2019 | Persen et al. | |
| 2019/0336020 A1 | 11/2019 | Kranz | |
| 2020/0113454 A1 | 4/2020 | Wu et al. | |
| 2020/0315480 A1 | 10/2020 | Hwang | |
| 2020/0375493 A1 | 12/2020 | Kranz | |
| 2021/0113136 A1 | 4/2021 | Bojovic et al. | |
| 2021/0137392 A1 | 5/2021 | Hwang | |
| 2021/0169392 A1 | 6/2021 | Albert et al. | |
| 2021/0267525 A1 | 9/2021 | Albert | |
| 2022/0015653 A1 | 1/2022 | Persen et al. | |
| 2022/0015679 A1 | 1/2022 | Shvilkin et al. | |
| 2022/0015680 A1 | 1/2022 | Vajdic et al. | |
| 2022/0039726 A1 * | 2/2022 | Vlaskalic | A61B 5/0006 |

(56) References Cited

U.S. PATENT DOCUMENTS

| | | | |
|---|---|---|---|
| 2022/0386929 | A1 | 12/2022 | Persen et al. |
| 2023/0414150 | A1 | 12/2023 | Shvilkin et al. |
| 2024/0023817 | A1 | 1/2024 | Vajdic et al. |

FOREIGN PATENT DOCUMENTS

| | | |
|---|---|---|
| CN | 101524272 A | 9/2009 |
| CN | 202854760 U | 4/2013 |
| CN | 203000927 U | 6/2013 |
| CN | 105147274 A | 12/2015 |
| CN | 106691423 A | 5/2017 |
| EP | 1227752 A1 | 8/2002 |
| EP | 0944353 B1 | 11/2002 |
| EP | 1659936 A1 | 3/2005 |
| JP | H0391304 U | 9/1991 |
| JP | 2007195690 A | 8/2007 |
| KR | 20150083000 A | 7/2015 |
| WO | WO01/70105 A2 | 9/2001 |
| WO | WO2015/177594 A2 | 11/2015 |
| WO | WO2017/208040 A2 | 12/2017 |
| WO | WO2019/191487 A1 | 10/2019 |
| WO | WO2020/167154 A1 | 8/2020 |
| WO | WO2020/0232040 A1 | 11/2020 |

OTHER PUBLICATIONS

Belicev et al.; U.S. Appl. No. 17/948,099 entitled "Method and apparatus for reconstructing electrocardiogram (ECG) data," filed Sep. 19, 2022.

Vajdic; U.S. Appl. No. 18/068,481 entitled "Apparatus for generating an electrocardiogram," filed Dec. 19, 2022.

Vajdic et al.; U.S. Appl. No. 18/363,685 entitled Electrocardiogram patch devices and methods, filed Aug. 1, 2023.

Vajdic et al.; U.S. Appl. No. 18/608,813 entitled "Apparatus for generating an electrocardiogram," filed Mar. 18, 2024.

Dower et al.; A clinical comparison of three vog lead systems using resistance-combining networks; American Heart Journal; 55(4); pp. 523-534; Apr. 1958.

Goff et al.; 2013 ACC/AHA guideline on the assessment of cardiovascular risk: a report of the American College of Cardiology/American Heart Association Task Force on Practice Guidelines; Journal of the American College of Cardiology; 63(25 Part B); pp. 2936-2959; Jul. 1, 2014.

Goff et al.; 2013 ACC/AHA guideline on the assessment of cardiovascular risk: a report of the American College of Cardiology/American Heart Association Task Force on Practice Guidelines; Journal of the American College of Cardiology;; 129(25 Suppl 2): pp. S49-S73; Jun. 2014.

Kligfield et al.; Recommendations for the standardization and interpretation of the electrocardiogram: Part I: The Electrocardiogram and Its Technology a Scientific Statement From the American Heart Association Electrocardiography and Arrhythmias Committee, Council on Clinical Cardiology; the American College of Cardiology Foundation: and the Heart Rhythm Society Endorsed by the International Society for Computerized Electrocardiology; 49(10); pp. 1109-1127, Mar. 13, 2007.

Marma et al.; Systematic examination of the updated Framingham heart study general cardiovascular risk profile; Circulation; 120(5): pp. 384; Aug. 1, 2009.

Med-Tech Innovation; The ECG device the of a credit card; Aug. 23, 2017; retrieved from the internet (https://www.med-technews.com/news/the-ecg-device-the-size-of-a-credit-card/) on Jan. 26, 2021.

Perk et al.; European Guidelines on cardiovascular disease prevention in clinical practice (version 2012) The Fifth Joint Task Force of the European Society of Cardiology and Other Societies on Cardiovascular Disease Prevention in Clinical Practice; European heart Journal; 33(13); pp. 1635-1701; Jul. 1, 2012.

Rakshit et al.; EKF with PSO technique for delineation of P and T wave in electrocardiogram (ECG) signal; in 2015 2nd International Conference on Signal Processing and Integrated Networks (SPIN); IEEE; pp. 696-701; Feb. 19, 2015.

Sun et al.; Characteristic wave detection in ECG signal using morphological transform; BMC cardiovascular disorders; 5(1); pp. 1-7; Dec. 2005.

Belicev et al.; U.S. Appl. No. 17/494,806 entitled "Method and apparatus for reconstructing electrocardiogram (ECG) data," filed Oct. 5, 2021.

Vajdic et al.; U.S. Appl. No. 17/570,368 entitled "Electrocardiogram patch devices and methods," filed Jan. 6, 2022.

Vajdic ; U.S. Appl. No. 17/726,497 entitled "Apparatus for generating an electrocardiogram," filed Apr. 21, 2022.

Blanco-Velasco et al.; ECG signal denoising and baseline wander correction based on the empirical mode decomposition; Computers in biology and medicine; 38(1); pp. 1-13; Jan. 1, 2008.

Marouf et al; Algorithm for EMG noise level approximation in ECG signals; Biomedical Signal Processing and Control; vol. 34; pp. 158-165; Apr. 1, 2017.

Kikillus et al; Three different algorithms for identifying patients suffering from atrial fibrillation during atrial fibrillation free phases of the ECG; Computers in Cardiology; IEEE; pp. 801-804; Sep. 2007.

Meredith et al.; Photoplethysmographic derivation of respiratory rate: a review of relevant physiology; Journal of Medical Engineering and Technology; doi:10.3109/03091902.2011.638965; pp. 60-66; Mar. 2012.

Park et al.; Real-time estimation of respiratory rate from a photoplethysmogram using an adaptive lattice notch filter; Biomedical Engineering Online; 13:170; pp. 1-7; Dec. 2014.

Persen et al.; U.S. Appl. No. 16/035,568 entitled "Systems, methods, and computer software for health monitoring and guidance," 31 pages, filed Jul. 13, 2018.

Pirhonen et al.; Acquiring respiration rate from photoplethysmographic signal by recursive bayesian tracking of intrinsic modes in time-frequency spectra; Sensors; 1896); doi:10.3390/s18061693; 16 pages; May 2018.

Sioni et al.; Stress detection using physiological sensors; Computer; 48(10); pp. 26-33; 12 pages; Oct. 2015.

Atanasoski et al.; U.S. Appl. No. 18/595,410 entitled "Methods and apparatus for electromyography noise elimination from electrocardiogram signals by iterative regeneration," filed Mar. 4, 2024.

Bartolo et al.; Analysis of diaphragm EMG signals: comparison of gating vs. subtraction for removal of ECG contamination; Journal of applied physiology; 80(6); pp. 1898-1902; Jun. 1, 1996.

\* cited by examiner

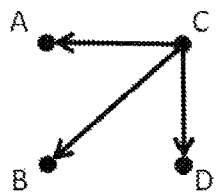 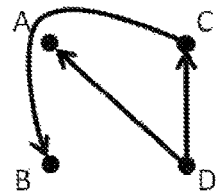 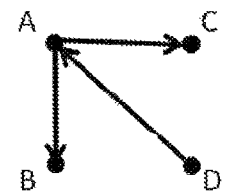
FIG. 11E  FIG. 11F  FIG. 11G
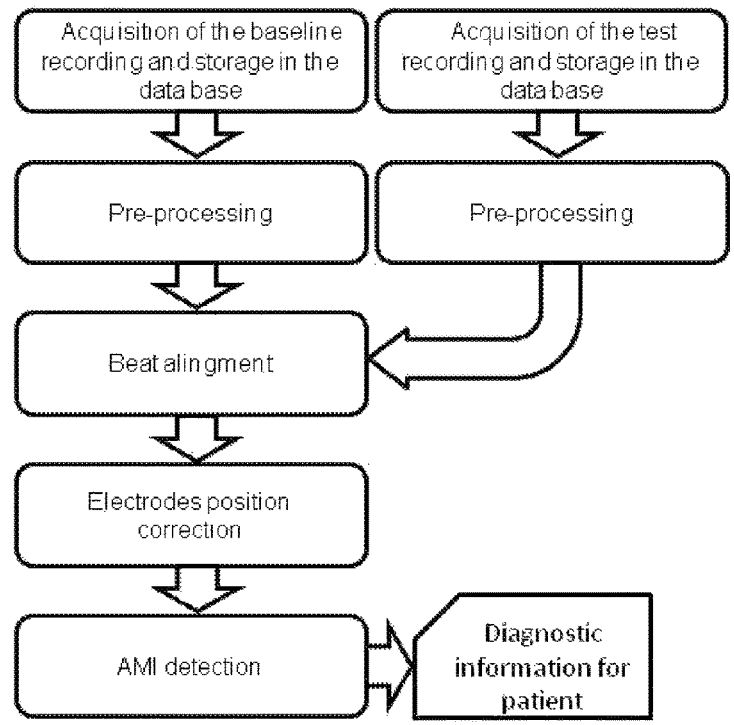
FIG. 12
| Risk factors | Risk level | | | | | | | | | | | | | | | | | | | | | | | | | | |
|---|---|---|---|---|---|---|---|---|---|---|---|---|---|---|---|---|---|---|---|---|---|---|---|---|---|---|---|
| Combinations | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| 1.Pre existing risk (PER) | H | H | H | H | H | H | H | H | H | I | I | I | I | I | I | I | I | I | L | L | L | L | L | L | L | L | L |
| 2. Chest pain (CPR) | H | H | H | I | I | I | L | L | L | H | H | H | I | I | I | L | L | L | H | H | H | I | I | I | L | L | L |
| 3. HB marker (HBR) | H | I | L | H | I | L | H | I | L | H | I | L | H | I | L | H | I | L | H | I | L | H | I | L | H | I | L |
| Post test AMI risk (PTR) | H | H | H | H | H | I | H | I | L | H | H | H | H | I | L | H | L | L | H | H | I | H | I | L | H | L | L |
FIG. 14

| | | | |
|---|---|---|---|
| 1.1 | Location: Exclusive* | Substernal | 3 |
| 1.2 | | Precordial | 2 |
| 1.3 | | Neck, Jaw, Epigastrium | 1 |
| 1.4 | | Left chest | -1 |
| 1.5 | | Right chest | 1 |
| 1.6 | | Back | 0 |
| 1.7 | | Other | 0 |
| 2.1 | Pain area size: Exclusive | Less than a coin | -1 |
| 2.2 | | More than a coin | 1 |
| 3.1 | Radiation: Exclusive | Left or right arm | 2 |
| 3.2 | | Both shoulders or right shoulder | 3 |
| 3.3 | | Left Shoulder, or back, or neck, or lower jaw | 1 |
| 3.4 | | Abdomen, or lower back | -1 |
| 3.5 | | Other | 0 |
| 3.6 | | None | 0 |
| 4.1 | Characteristics: Exclusive | Crushing, pressing, squeezing | 3 |
| 4.2 | | Heaviness, tightness | 2 |
| 4.3 | | Burning/aching | 1 |
| 4.4*** | Only for pts with CHD, angina | Similar or worse than previous angina | 3 |
| 4.5 | | Sticking, stabbing, catching, pinprick | -1 |
| 4.6 | | Other | 0 |
| 5.1 | Aggravated by : Exclusive | Gets worse with exertion, makes you stop/slow down | 2 |
| 5.2 | | Gets worse with deep breath, cough | -1 |
| 5.3 | | Constant, not changing | 0 |
| 6.1 | Associated symptoms: Additive** | Nausea or vomiting | 2 |
| 6.2 | | Dyspnea | 2 |
| 6.3 | | Diaphoresis | 3 |
| 6.4 | | None | 0 |
| 7.1 | Duration : Exclusive | Intermittent (momentary) or < 2 min at a time | -1 |
| 7.2 | | 2-15 min | 1 |
| 7.3 | | 15-60 min | 1 |
| 7.4 | | 60 min – 12 hrs | 0 |
| 7.5 | | > 12 hrs | -1 |
| 8..1 | Frequency : Exclusive | >=2 per 24 hrs | 1 |
| 8.2 | | 1 or less per 24 hrs | 0 |
| 9.1 | Additional characteristics: Exclusive | Reproduces or worsens by palpation | 1 |
| 9.2 | | Not sensitive on palpation | 0 |

*exclusive – only single answer
**additive – multiple answers
*** 4.4 might be chosen with one of the other options of group 4.

FIG. 13

COMPACT MOBILE THREE-LEAD CARDIAC MONITORING DEVICE

CROSS REFERENCE TO RELATED APPLICATIONS

This patent application is a U.S. national phase application under 35 USC 371 of International Patent Application No. PCT/US2020/032556, filed on May 13, 2020, titled "COMPACT MOBILE THREE-LEAD CARDIAC MONITORING DEVICE" now International Publication No. WO 2020/232040, which claims priority to U.S. provisional patent application No. 62/847,308, filed on May 13, 2019, titled "COMPACT MOBILE THREE-LEAD CARDIAC MONITORING DEVICE."

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses (e.g., systems, devices, etc.) described herein may relate generally to electrocardiography. Described herein are apparatuses including compact, hand-held electrocardiogram (ECG) devices with foldable electrodes and systems and methods that may use them. In addition to recording of ECG signals these devices may process and transmit ECG data to a hand-held processor (e.g., a smart phone) and/or transmit the ECG data to a remote computer server for automated analysis and generation of diagnostic information that is returned to the patient and/or sent to a medical professional.

BACKGROUND

Hand-held ECG devices have been proposed. Such devices may be used by a patient (or a medical professional) to record an ECG. However, to date, despite the potential benefit to such hand-held apparatuses, none have found widespread use. This may be due in part, to the relatively large size, weight and complicated form factor for proposed devices, which may include a handle and/or a number of cables. Additionally, many such proposed devices have parts that are protruding out of the outer contours of the device when device is not in use. Therefore there is a need for a hand-held ECG that is capable of diagnosis of wide range of cardiac conditions, and that is on the other hand compact and easy to hold and carry in a pocket or wallet.

Described herein are apparatuses and methods that may address these issues.

SUMMARY OF THE DISCLOSURE

The present invention relates methods and apparatuses including compact and lightweight, hand-held ECG apparatuses, that may be easy to carry and handle, including by sliding it into a pocket or a wallet. These apparatuses may further be ergonomical, easy to use, and may be capable of detecting various cardiac pathological conditions.

For example, described herein are credit-card like mobile three-lead cardiac monitoring apparatuses for self-recording of ECG. These devices may be compact, e.g., having a maximum thickness in a stored configuration of 2 cm or less (e.g., 1.9 cm or less, 1.8 cm or less, 1.7 cm or less, 1.6 cm or less, 1.5 cm or less, 1.4 cm or less, 1.3 cm or less, 1.2 cm or less, 1.1 cm or less, 1.0 cm or less, etc., including between 0.2 and 2.2 cm, between 0.2 and 2 cm, etc.). These devices may also be easy to handle and at the same time lightweight, making them easy to carry and hold when not in use, yet effective in detection and diagnosis of various heart conditions.

Thus, described herein are compact, hand-held ECG devices for recording and analyzing a patient's ECG without using cables. In some variations, the credit card like (e.g., relatively thin, and have a small diameter, e.g., having a maximum diameter of 12 cm or less (e.g., 11 cm or less, 10 cm or less, 9 cm or less, 8 cm or less, etc.). These apparatuses may be highly mobile and may be configured to provide three-lead cardiac monitoring; the apparatus may include two electrodes for contacting the patient's chest and two electrodes for contacting the patient's fingers. The finger electrodes may be integrated at the front and/or sides of the device.

For example, the four recording electrodes may be on a front face and may be on two pivotable arms so that when the device is in operating position it may be held by both of the user's hands in a predefined orientation, so as to record 3 orthogonal lead cardiac signals when held against the user's chest. Examples of orthogonal lead recordings are described in patent document WO2016/164888A1, herein incorporated by reference in its entirety.

In some variations, the apparatus may be operated by a patient experiencing symptoms related to an ongoing cardiac event and may be used with, or as part of a system, configured for automatic or semi-automatic detection and diagnosis of acute myocardial infarction (AMI), atrial fibrillation or other heart disorders by acquiring three substantially orthogonal leads from the four integrated electrodes, which may be used to generate a heart vector that may be further used, e.g., as part of a differential vector analysis of the heart vector, to detect one or more cardiac events. The differential heart vector may be used with additional information, including risk factor information and current symptom information, to further refine a patient's immediate condition, e.g., to determine or confirm that a patient is experiencing a cardiac event.

The three orthogonal leads may be formed by using different electrode configurations with or without a resistive network having a central point. The resulting three leads are typically non-coplanar, and as close to orthogonal as possible.

In some variations, the apparatus (system, device, etc.) may perform a baseline recording of the first set of three orthogonal leads that may be stored in a memory (e.g., register). During diagnostic recording, a second set of three orthogonal leads may be taken, and a difference signal between the two sets may be determined. The recorded cardiac signals represented by the parameters of ECG baseline recording, diagnostic recording and difference signal may be transmitted to an internal processor and/or may be wirelessly transmitted to a remote processor for processing. The device may also be configured for communicating the diagnostic information by the device to the patient. The received diagnostic information may be presented to the user in a form of characteristic sound, voice, graphics or text.

For example, the apparatus may include a plate-like casing having a front and/or a rear face. The casing may have a size and shape similar to a typical credit card. The casing may be provided with two pivotable arms disposed on either side thereof, each arm being provided with an electrode may acquire signals relating to the patient's chest. The arms may be folded down in respective compartments provided in the casing so that they fit flush to the external surfaces of the casing when not in use, for example during transport (e.g., in a compact configuration).

Furthermore, the arms may comprise locking means for locking the arms against the casing when held in folded down position, so that the arms are locked relative to the casing in a spring-loaded manner. The arms may be provided with a bias (e.g., an elastic, a spring, etc.) for spring loading the arms for release from a folded-down position; alternatively the arms may be biased to be held down in the collapsed configuration. The bias may be unloaded when the arms are unfolded. The arms may be locked in the collapsed configuration (and biased to expand when the lock is released) and/or may be locked in the expanded configuration (and in some variations biased to collapse into the compact configuration when the lock is released). For example, there may be provided a respective torsion spring associated with each of the arms, such that the end portions of each torsion spring are being supported at the arm and the casing respectively.

The pivotable arms may provide a compact size when retracted in their respective compartments; when unfolded, the arms may extend in an operating position forming an angle therebetween and are therefore capable of adapting to the patient's chest morphology and producing good contact between the associated chest electrodes and the patient's skin. The distance between chest electrodes in the deployed (e.g., operating) position may be more than 10 cm. In some variations, the deployed configuration may extend the arms and associated electrodes beyond the edge of the casing.

In some variations the device may include two hand electrodes that are disposed on the front face and/or side of the casing. For example, these two electrodes may be disposed on the front face of the casing in such a manner as to enable the fingers of the patient to be applied on the two electrodes when the chest electrodes are in position on the chest of the patient. Advantageously, this may enable the patient to get a good grip on the device and to hold it securely for recording an ECG.

In some variations, these two 'hand' electrodes are disposed on a corresponding chamfered part of the front longitudinal edges of the casing. In this way the easy access by the patient's fingers is enabled, as well as a pressure needed for holding the casing against the chest. The hand electrodes may be offset relative to the transverse centerline of the front face, so that they are closer to the left arm of the patient during recording, in order to avoid finger switching between left and right hand by the patient.

In some variations, the hand electrodes may be disposed in the recessed portions of the front face of the casing to enable fitting the hand electrodes to be flush to the front face. In some variations the device may include, in addition to the two finger electrodes and two chest electrodes, a ground electrode disposed on the front face of the casing so as to be pressed by a finger, in the same manner as the recording hand electrodes.

For example, described herein are mobile three-lead cardiac monitoring device having a first compact and undeployed configuration and a second deployed configuration (e.g., "compact" devices). The device may include: a casing having a front face and a rear face; two chest electrodes; two finger electrodes; and two foldable arms pivotably attached to the casing on opposing ends thereof, wherein the two finger electrodes are disposed on the front face or a front edge of the casing and the two chest electrodes are disposed on the foldable arms, wherein the foldable arms are folded flush with the rear face in the undeployed configuration and extend at an angel to the rear face in the deployed configuration.

Also described herein are methods of using these mobile three-lead cardiac monitoring device having a first compact and undeployed configuration and a second deployed configuration as described herein. For example, described herein are methods of automatically assessing a patient's risk of an acute cardiac event, the method comprising: receiving, from the patient, risk assessment information comprising risk factors, wherein the risk assessment information is received by a processor; storing a pre-existing risk score based on the risk assessment information; receiving, from the patient, a sample electrocardiogram (ECG), wherein the patient self-records the sample ECG using a mobile three-lead cardiac monitoring device having a first compact and undeployed configuration and a second deployed configuration, and receiving, from the patient, a current symptoms indication; determining, in the processor, an ECG risk score from the sample ECG and a baseline ECG, and a chest pain risk score based on the current symptoms indication, and using the ECG risk score, the pre-existing risk score, and the chest pain risk score to determine a post-test risk score; and presenting, to the patient, a diagnostic report and patient action instruction based on the post-test risk score.

Any of these methods may include deploying the mobile three-lead cardiac monitoring device from the first compact and undeployed configuration into the second deployed configuration. For example, deploying the device may include releasing a lock so that the legs are automatically extended from out of a storage compartment. Deploying may include holding the legs against the chest. The configuration of the electrodes and/or the legs described herein may provide enhanced contact, comfort, and accuracy. The body of the device may be held separately from the chest, while allowing the electrodes to conform thereto.

These methods may include receiving in the processor, from the patient more than 24 hours before receiving the sample ECG, the baseline ECG, wherein the patient uses the hand-held apparatus to acquire the baseline ECG. The risk factors may include: age, total cholesterol, HDL, systolic blood pressure, diabetes mellitus status, and current smoking status. In some variations, the pre-existing risk score based on the risk assessment information comprises calculated a weighted sum of the risk factors.

Receiving the sample ECG may comprise the patient using the mobile three-lead cardiac monitoring device having a first compact and undeployed configuration and a second deployed configuration, wherein the hand-held apparatus has at least four electrodes, to acquire three substantially orthogonal leads. Receiving the current symptoms indication may comprise selecting the current symptoms indication from a predetermined list of symptom selectable on the hand-held apparatus. In any of these methods, selecting may comprise selecting from a user interface on the hand-held apparatus, the current symptoms indication. Determining the ECG risk score may comprise indicating a risk that is high (H), intermediate (I) or low (L). Determining the chest pain risk score may comprise indicating a risk that is high (H), intermediate (I) or low (L). For example, determining the post-test risk score may comprise applying a look-up table indexed by the ECG risk score, chest pain risk score and pre-existing risk score. The step of receiving the sample ECG and the current symptoms indication may be repeated prior to determining the ECG risk score

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 11E, 11F and 11G show schematic diagrams of three possible configurations for measuring 3 leads among two chest and two hand electrodes.

FIG. 12 shows a flow chart of the method for detecting AMI including with a mobile three-lead cardiac monitoring device having a first compact and undeployed configuration and a second deployed configuration as described herein.

FIG. 13 is a table illustrating a list of parameters-questions that may be used to estimate chest pain risk (CPR) as described herein.

FIG. 14 is a table illustrating one example of a method of assessing AMI risk as described herein.

DETAILED DESCRIPTION

Figure 1:
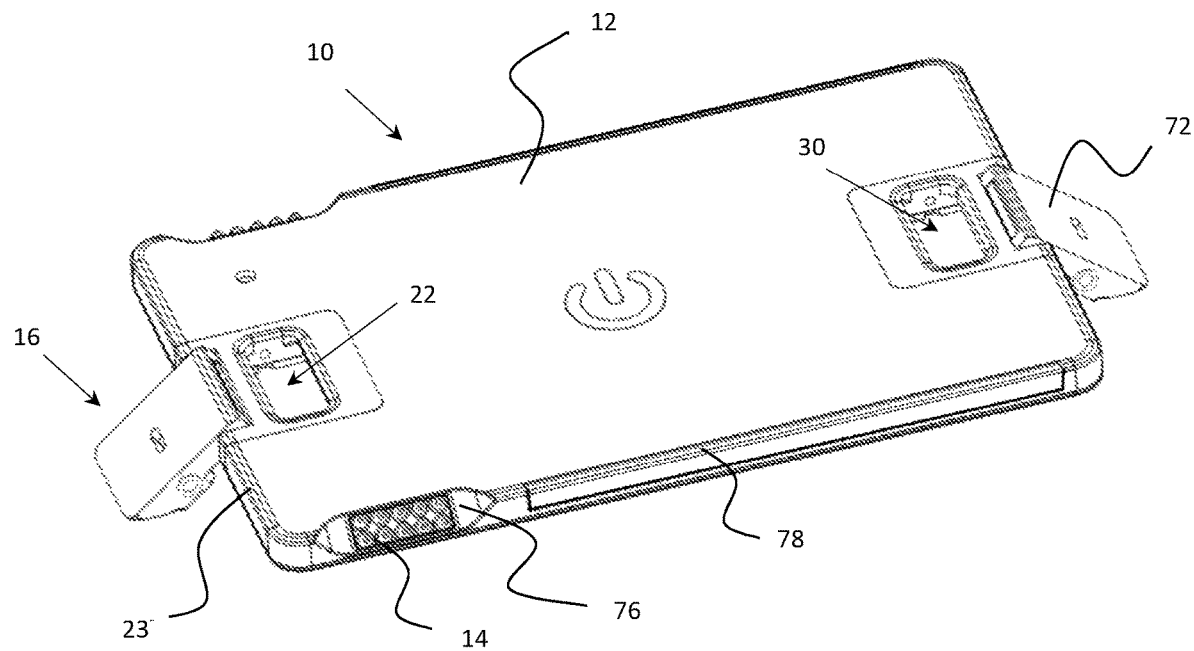
FIG. 1 shows a front axonometric view of the device with the arms in unfolded position when the device is ready to be used for ECG recording.
Figure 2:
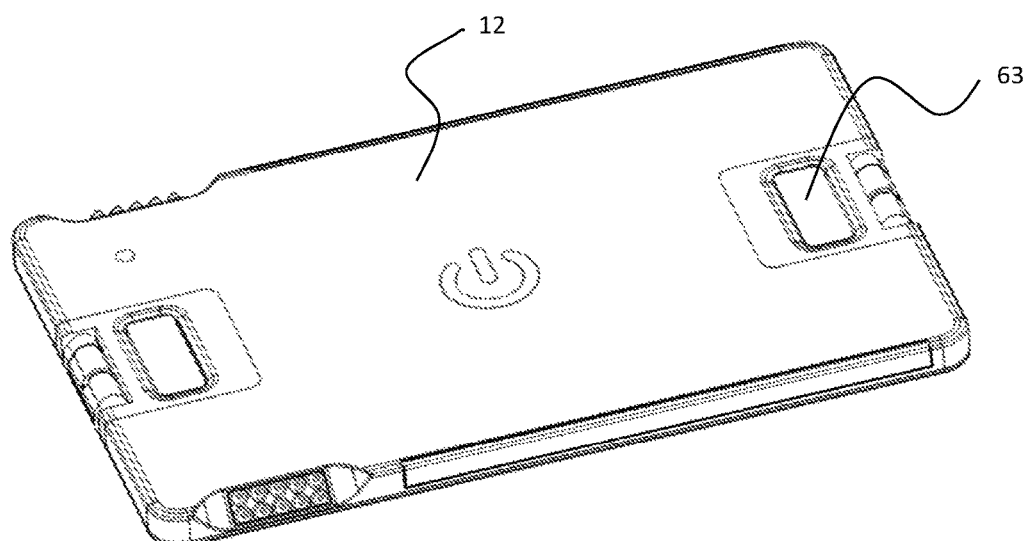
FIG. 2 shows a front axonometric view of the device in transport position with the arms folded into compartments of the casing, e.g. when the device is not in operation.
Figure 3:
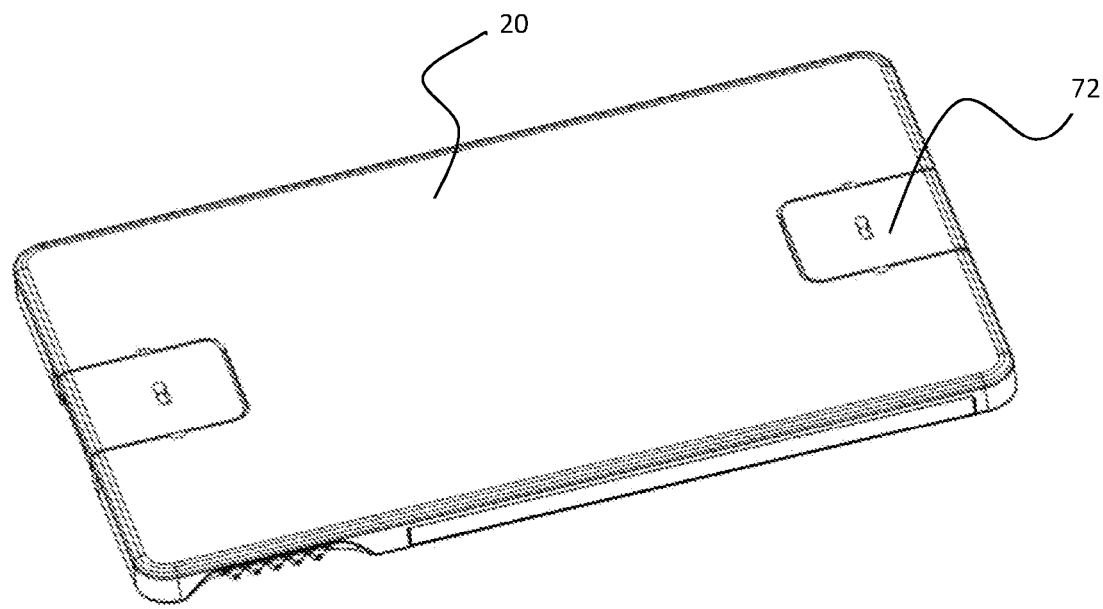
FIG. 3 is a rear axonometric view of the device with the arms in a folded-down position.
Figure 4:
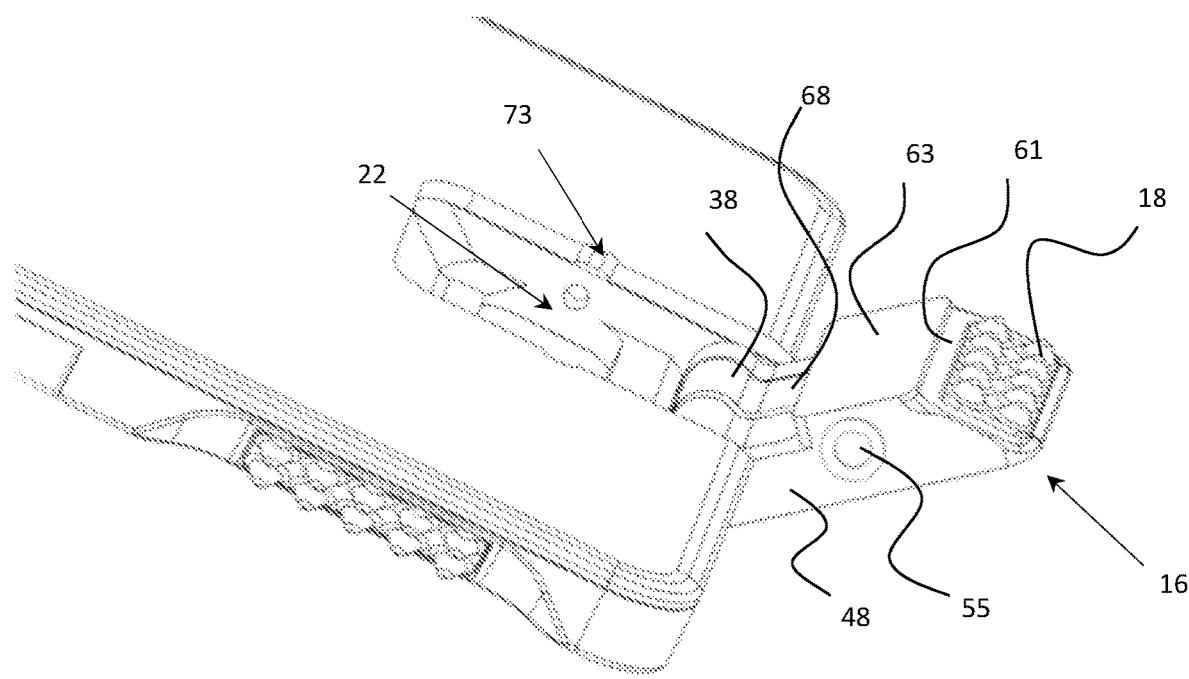
FIG. 4 is a detail showing an axonometric view of arm and compartment seen from behind, in unfolded position.
Figure 5:
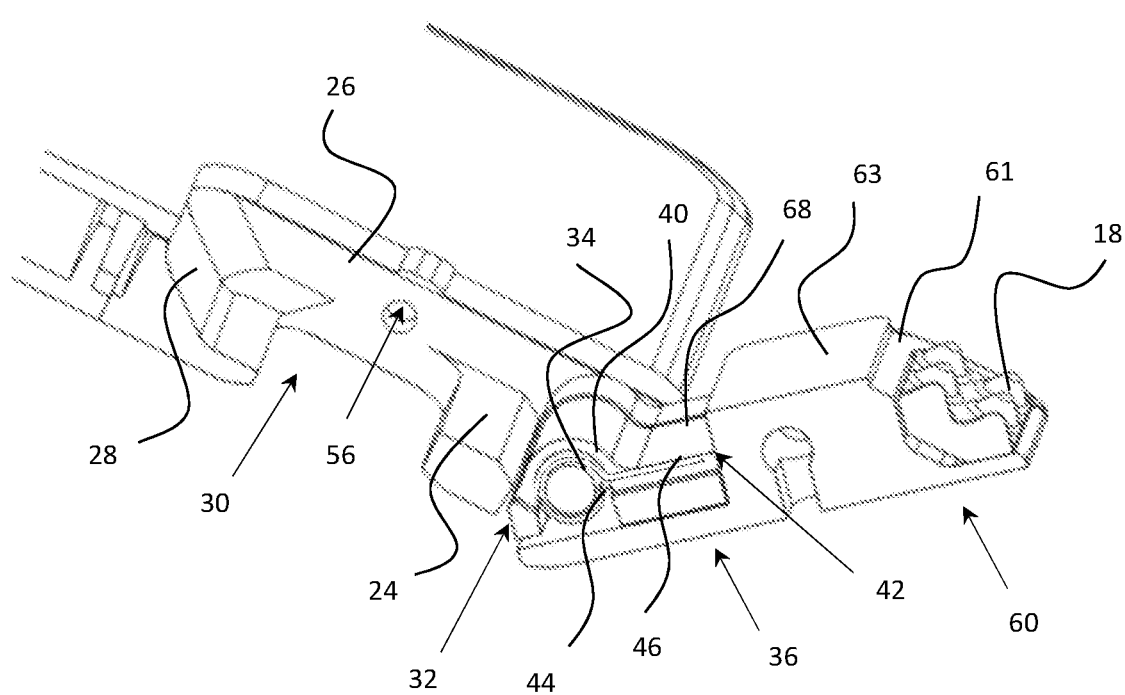
FIG. 5 shows an axonometric longitudinal section of the view of FIG. 4.

Described herein are apparatuses, including devices and systems that may include compact (e.g., credit card size and shaped) mobile three-lead cardiac monitoring devices for user placement on the chest. These devices may have four recording electrodes arranged to enable recording of three orthogonal ECG lead signals. These hand-held devices may include two recording chest electrodes disposed on pivotable and/or retractable arms hinged at the casing of the device. The device may include two non-chest electrodes disposed on the front face and/or side (including a chamfered side) of the casing which may be used for collecting cardiac signals from the fingers of the right and left hand. The device may also have an optional fifth electrode disposed at the front face of device, which may be used as the ground electrode, so that the device includes four recording electrodes and one ground electrode.

The apparatuses described herein may be used for automatic remote diagnostics of cardiac conditions, such as acute myocardial infarction (AMI), atrial fibrillation (AFib), or the like, for example in the case of a supposed cardiac event. The device is configured to measure three cardiac leads that are substantially orthogonal and contain the majority of diagnostic information that is present in the conventional 12-lead ECG as well as ECG recording components (e.g., electrodes, circuitry, controller) for recording a patient's ECG signals.

FIGS. 1-4 show one example of a device (a credit-card like hand-held ECG device) as described herein. The device may include a plate-like casing whose thickness is relatively small compared to its length and width. The shape of the casing may be similar to that of a typical credit card, such that the base of the casing has approximately the same length and width of the standard credit card, e.g., a length of between about 6 and 10 cm (e.g., between about 7 and 9 cm, between about 7.5 and 9 cm, between about 8.2 and 8.8 cm, about 8.6 cm) and a width of between about 4 cm and about 6.5 cm (e.g., between about 4.5 cm and about 6.5 cm, between about 5 and about 6 cm, between about 5.2 and 5.8 cm, etc., such as about 5.4 cm), respectively. The device casing may be thinner than 10 mm (e.g., about 8 mm or less, about 7 mm or less, about 6 mm or less, about 5 mm or less, about 4 mm or less, etc.) on average.

In some variations, the casing 10 has a face 12 (e.g., a front face) provided with hand electrodes 14 for collecting signals from the patient's hands and two pivotable arms 16 hinged at the casing 10, each arm being provided with a chest electrode 18 for collecting signals from the patient's chest. The casing 10 may be made of plastic or metal.

Additionally, the casing 10 may have a face 20 (e.g., a rear face) that is recessed so that two substantially prismatic compartments 22, one opposed another, are positioned symmetrically along the longitudinal center line of the rear face 20, each compartment 22 being formed adjacent to the shorter edge 23 of the front face.

Each compartment has bottom 24, two lateral walls 26 and a front wall 28. Unlike lateral walls 26 that are perpendicular to the bottom 24, the front wall 28 is inclined with respect to the bottom 24, preferably at an angle of about 45 degrees, so that the compartments 22 expand outwardly from the bottom up.

In the bottom 24 of the compartment 22, along the longitudinal center line there are formed two substantially rectangular openings 30, 32 that are spaced apart. The proximal opening 30 is adjacent to the inclined front wall 28, whereas the distal opening 32 is positioned at the shorter edge of the front face 12 in such manner that it has an open end. The distal ends of the lateral walls 26 are connected by a pin 34.

The compartments 22 may receive two pivotable arms 16 hinged to the casing 10 via pins 34 disposed at the compartments 22. On its tail portion 36 each arm has an integrally formed sleeve 38, whereas a coiled torsion spring 40, is disposed in a slot 42 formed in the arm 16, in such a manner as to be coaxial with the sleeve 38. The torsion spring 40 includes with two radially projecting tangs 44, 46. A first tang 44 engages the arm 16 and the second tang 46 engages a pin 34 in the compartment 22. When the arm is folded, the first tang 44 is moved angularly relative to the second tang 46, causing torsional loading of the spring 40. The arm 16 is mounted together with the spring 40 on the pin 34 with a close fit. Since each arm 16 is pivotable around the respective pin 34, the arms are capable of being received in the compartments 22 or being unfolded so as to form an angle of about 135 degrees therebetween.

The arms may be biased to open and/or close. For example, two spring plungers may be included inside the arm 16, perpendicular to sides 48. The plungers may be slidebly displaceable in an associated cylinder, such that the tips 55 of the plungers may point outwards when the spring is unloaded. The tips 55 of the plungers may engage in a biased (e.g., spring loaded) manner with corresponding sockets 56 formed in the lateral walls 26 of the compartments 22 in order to releasably lock the arms 16 and hold them by a spring force against the lateral walls 26 in a folded down state. Thus, the lateral walls 26 of the compartment 22 and the arms 16 in this example are loaded against one another via a retaining spring. The spring force and the shaping of the socket 56 define the threshold force required to compress the spring 52 and release the tips 55 of the plungers from the socket 56 and thereby to unlock the arms 16. The cooperation of tips 55 and sockets 56 assures secure holding of the arms 16 when they are folded down in a pocket or wallet by user.

The accommodation of the arm 16 in the compartment 22 is enabled by providing the arm 16 of stepped prismatic shape, complementarily conforming to the shape of the compartment 22, when the arms 16 are in folded down position.

Each arm 16 includes a head portion 60 that tapers at its distal end forming a recessed face 61 for accommodating the recording chest electrode 18. The face 61 is inclined at an angle of about 45 degrees with respect to the top side 63 of the head portion 60, so as to be parallel to the front and rear faces 12, 20 of the casing when the arms 16 are in unfolded position and parallel to the compartment's inclined front wall 28, when the arms 16 are received in the compartment 22 in folded down position. The arm 16 is stepped so that the top side 68 of the tail portion 36, is lower relative to the top side 63 of the head portion 60.

The head portion 60 of the arm 16 has a rectangular base section shaped to be received in the rectangular opening 30 of the compartment 22 when the arms are folded down. At the same time the top side 63 of the head portion 60 and the bottom side 72 of the arms 16 fit flush to the front and rear faces 12, 20 of the casing 10, respectively. In this way, the most compact size of the device is achieved, when it is not being used.

The openings 30 in the bottom 24 of compartments 22 enable access to the arms 16 by the patient's fingers from the front side so that enough pressure can be produced by pressing with fingers to unlock the arms by pushing the top sides 63 of the head portions 60 of the arms 16 and bringing the arms 16 in unfolded position. The top side 63 of the head portions 60 of each arm is distinctively colored so it enables operation even when visibility is lower.

Four semicircular recesses 73 are provided at the rear face 20 such that each recess 73 is positioned over and adjacent to respective socket 56, adapted to receive the tip 55 of the plunger before it engages with the socket 56.

The two recording chest electrodes 18 disposed at the arms 16 are used to make contact with the chest of the patient in the recording position. When the arms 16 are unfolded in operating position the two chest electrodes 18 may be arranged to cover distance greater than about 10 cm in caudal direction. The reason for having such spaced arrangement is to advantageously achieve the distance greater than approximate diameter of the heart muscle which is needed to achieve lead orthogonality as much as possible.

In addition, pivoting arms 16 and bringing them in the unfolded operating position enable achieving good contact with the patient's chest regardless of morphology of the patient's torso, since the angle between the arms follows the curvature of different body shapes.

According to some variations, in addition to the two chest electrodes, the device further includes two recording hand electrodes 14 disposed on chamfered portions 76 of the longer front edges 78 of the device front face 12 so as to be easily accessible by the fingers. The finger electrodes are used for acquiring cardiac signals from the fingers of the right and left hand by pressing preferably with the patient's thumbs.

According to an alternative embodiment the device may include a third electrode disposed at the front face, so as to be pressed by a finger, used as the ground electrode. By pressing with the fingers the non-chest electrodes mounted on the front face 12 of the casing 10 enough pressure is produced to hold the device against the chest.

The recording electrodes 14, 18 are made up of profiled biocompatible plastic material with spherical protrusions that enable effective grip with the patient's chest and fingers and ensure holding the device securely in place. For operation, the user (e.g., patient) positions and presses the device against his chest e.g., with his both hands, including with his thumbs, so that each thumb touches one hand electrode 14, whereby the chest electrodes 18 contact his chest for producing tight contact between chest and the device. This may produce enough pressure for holding the device against the chest.

In order to prevent wrong positioning of the device, according one embodiment, the hand electrodes 14 are offset relative to the transverse centerline of the front face 12 in order to provide asymmetric electrode configuration. Namely, during the recording, the side of the front face 12 where the hand electrodes 14 are disposed is oriented towards patient's head. In this way, the upper and lower side of the device can be easily distinguished by the patient.

In an optimal recording position the center of the device is placed closely above the center of the heart so that the chest electrodes are approximately on the midclavicular line (the vertical line passing through the midpoint of the clavicle bone), and the lower chest electrode is at about the level of the lower end of the sternum.

Furthermore, in an alternative embodiment hand electrodes may be disposed instead of on chamfered portions of front longer edges of the casing, on the front face of the casing, so as to be easily accessible and touched by digit fingers. The electrodes for recording ECG signals of the right and left arm by pressing with digit fingers of the right and left hand may be disposed in the recessed portions of the front face, instead on the tapered portions of the front longer edges, as described above, so that they fit flush to the front face.

Active recording electrodes for recording ECG signal of the patient's chest are disposed on the pivotable arms of the device in the same manner as described above. In the recording position, the chest electrodes are pressed against the chest, in the manner equivalent to the one shown above.

In another alternative embodiment, an additional electrode, serving as a ground electrode, may be disposed on the front face of the casing so as to be touched by any of the free fingers, simultaneously, as the device is pressed against the chest by pressing the finger recording electrodes. The ground electrode may serve to produce additional force needed to hold device against the chest to perform accurate recording and may be preferably made up of profiled biocompatible plastic material with spherical protrusions to enable effective grip with the patient's fingers to ensure holding the device securely in place.

The optimal position of the hand-held device on the chest is with center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum.

The hand-held devices described herein are configured to be mechanically stable and allow good electrical contact with the chest and to eliminate possibility for switching of finger contacts. In order to prevent turning the device upside down during the recording procedure, so that the upper side is facing toes of the patient, instead of facing his head, which would lead to a useless recording, either upper or front side of the device may be clearly identified and/or formed, (including being marked) to be easily distinguishable by the patient, for example by integrating a LED diode, in the upper front surface of the device casing, indicating the current phase of recording. In addition, the upper (facing head) and lower part (facing toes) of the device may be easily distinguished, since turning the device upside down would lead to wrong recording.

In some variations a four recording electrode configuration (e.g., having two chest and two finger electrodes) without the ground electrode is used. This configuration may give acceptable 50-60 Hz electrical noise performance if a ground-free signal amplifier configuration is used. This recording electrode configuration may also fulfill the condition of high orthogonality. The simplest way to fulfill this requirement may be to record signals in three main body directions: lateral (left arm-right arm), sagittal (back-front) and caudal (head-toes). For example, the signal in the lateral direction may be obtained by measuring the lead between left and right hand. The signal in the caudal direction may be obtained by measuring the lead between the two chest electrodes, with the condition that the distance between the chest electrodes in caudal direction is at least 5 cm, preferably greater than about 10 cm, in order to be greater than the approximate diameter of the heart muscle. In an ideal case, the signal in the sagittal direction would be measured between the back and the chest of the patient, which is not possible with the constraint of using only finger and chest electrodes. To overcome this, we use a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kOhm (kΩ) each, or unequal, the first one approximately 5 kOhm (kΩ) between the left-hand electrode and the CP, and the second one approximately 10 kOhm (kΩ) between the right hand electrode and the CP. This asymmetry reflects the left-side position of the heart in the torso, thus shifting the CP at the approximate electrical center of the heart. In this way, we obtain a three lead system that are substantially orthogonal. Other lead configurations with or without CP may also be used.

The hand-held cardiac device is configured as a stand-alone device incorporating a cardiac signal recording circuitry including amplifiers and AD convertor for amplifying the signals detected by the electrodes, data storage circuitry (e.g., memory) for storing the recording signal, communication circuitry operating on GSM, WWAN, or a similar telecommunication standard for communication with the remote processor (e.g., PC computer, pad, smartphone, etc.) and circuitry (e.g. screen, speaker, etc.) for communicating diagnostic information to the user in the form of visual and/or audio output.

The hand-held device with special electrode configurations is capable of recording three orthogonal cardiac lead signals in an orientation-specific manner, and transmitting these signals to a processor (e.g., PC or other computing device). The remote processor may be configured to diagnose/detect AMI and transmit the diagnostic information back to the hand-held device.

Each user may be registered in the diagnostic system by performing the first transmission of his/her non symptomatic cardiac recording with three cardiac leads. This first recording may be used as a reference baseline recording for AMI detection in the diagnostic recording (diagnostic recording meaning any further recording of the three cardiac leads of the same user). The availability of the reference baseline cardiac recording may allow distinguishing new from old ST elevation (STE), or equivalent parameter, and also other cardiac signal changes suggesting an AMI, providing a tool for automated AMI detection that may have diagnostic accuracy comparable to human ECG interpreters.

The remote processor may be equipped with diagnostic software for processing the received cardiac signals, producing diagnostic information and for transmitting the information back to the hand-held device for communicating the diagnostic information to the patient. The device may be capable of performing automated detection of a cardiac condition on the basis of a 3-lead system and may not require interpretation of the processed diagnostic information by a specialist.

The signal processing and diagnostic software can also be run on the processor (e.g., microprocessor) integrated in the casing of the hand-held device for processing the recorded cardiac signals and producing diagnostic information. When the diagnostic processing is carried out by a remote processor, a backup version of the software running on the microprocessor may be integrated in the hand-held device, and may be used in situations when the user is in a zone without wireless network coverage The device may be communicating with the remote processor via integrated communication circuitry. The remote processor may communicate with the hand-held device via integrated communication module. The created diagnostic information may be transmitted from the remote processor (e.g., a PC computer, server, etc.) to the device memory via commercial communication network. The hand-held device may communicate the diagnostic information to the patient via characteristic sounds via microphone producing characteristic sounds, voice massages or in the form of graphical information via a display integrated in the device.

EXAMPLE

Figure 6A:
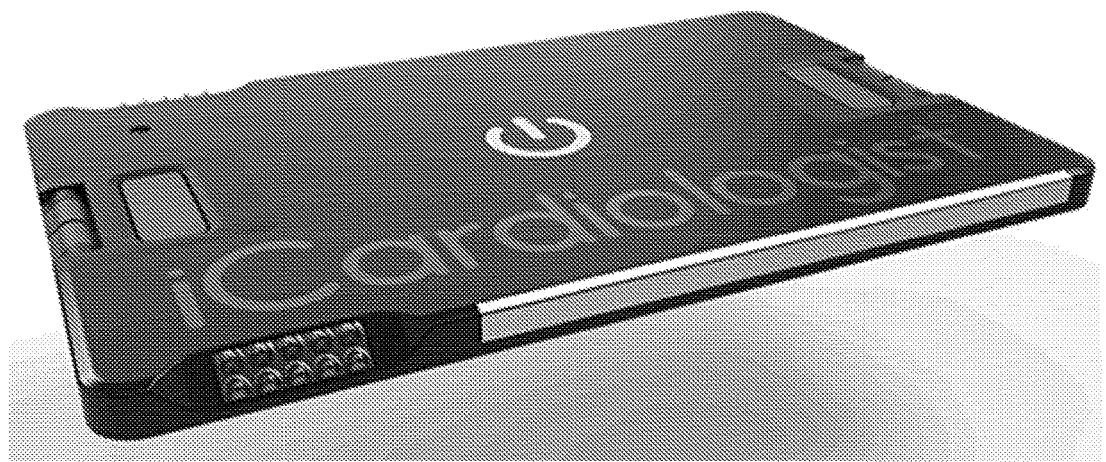
FIGS. 6A-6B illustrate prototype signal collection devices for recording an ECG.
Figure 6B:
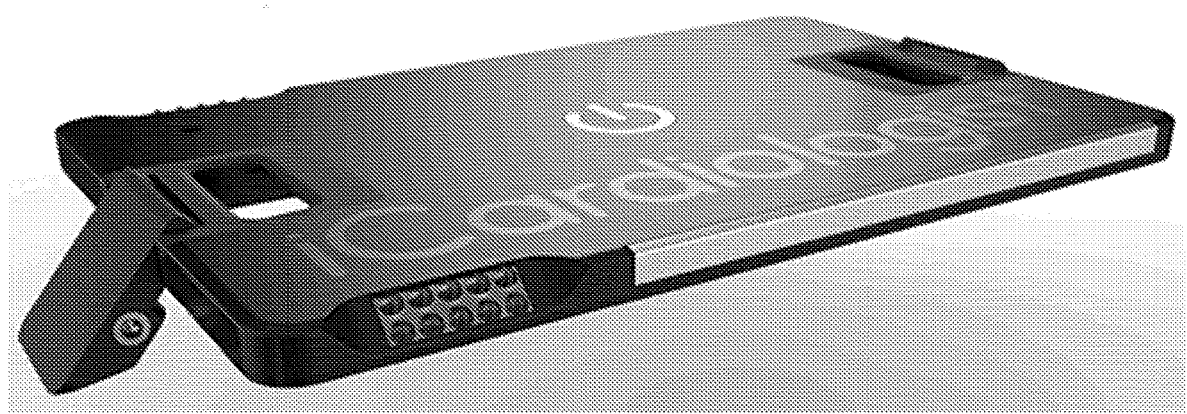

The devices described herein may be referred to as signal collection devices. FIGS. 6A-6B illustrate a prototype of an exemplary signal (ECG) collection device, shown in the compact configuration (FIG. 6A) and a deployed configuration (FIG. 6B), with the chest electrodes deployed.

In some variations the device may be used as part of a subscription service in which the patient signs up for a subscription plan, or is signed up for by their physician, insurer, etc., (e.g., a recurring service at x$/month) during which time they can record their own ECG when they are experiencing symptoms of a cardiac event; the system may provide report directly to the patient and/or to a physician that may communicate with the patient. The output (e.g., a patient or physician report) may include advice (go to ER, call physician, etc.). In some variations the report may include risk factors as well as the analysis of the heart vector and/or a representation of the ECG (including a synthesized ECG generated from the heart vector/orthogonal leads). In some variations the report may give an indication of high, low, intermediate (or the like) indicating likelihood of a cardiac event.

Alternatively, the report may be fully automated, with the system generating a score based on a differential comparison between the acutely measured heart vector (when the patient suspects that they are experiencing a cardiac event) and a baseline heart vector (e.g., measured from the patient when not experiencing a cardiac event, as vetted by the system. The system analysis engine may generate the score and send it directly to the patient, either to the hand-held signal collection device, and/or to a mobile device (e.g., smartphone) associated with the hand-held signal collection device.

Thus, any of the apparatuses described herein may include software or firmware that is either part of the signal collection device and/or is part of a mobile device (e.g., smartphone) that the signal collection device is in communication with. For example, described herein is an application (e.g., an "app") that may drive a processor of the signal collection device and/or a mobile communications device and may provide a user interface for operating the signal collection device, collecting patient data (e.g., risk factors), subscribing the patient, allowing the patient to use the signal collection device to collect one or more ECG, collect user symptom data associated with an ECG and/or report the results of the analysis. The application may also communicated securely between the signal collection device and a remote server (e.g., a cloud-based server) for analyzing and storing patient ECG data, risk factors and other associated data.

For example, in some variations the patient may use the app to take an ECG using the signal collection device; the patient may turn on the app and select new recording (either baseline or test/symptom ECG) and the app may walk the user through the recording. The signal collection device, in some variations, may wirelessly communicate with the mobile communications device running the app (e.g., via any wireless technique, in particular wireless personal area networks, including Bluetooth, etc.). When initialized, the app may look for the signal collection device, and may automatically turn it on (and later turn it off), either the signal collection device or the app (or a combination of both) may detect skin contact and may begin recording from the chest and finger electrodes. The recorded signal (from all of the three leads, including the virtual sagittal lead derived from a central point of the resistive network between the left and right hand electrodes as well as one of the chest electrodes, e.g., the lower chest electrode) may be processed at the signal collection device and/or at the application (e.g., smartphone), including processing to confirm sufficiently low noise and quality of data collected. The recorded signal(s) may be stored on the signal collection device and/or mobile communications device, when one is used, and later transmitted to the remote server. The signal collection device may include storage and/or the signal(s) may be stored on the patient's smartphone, then transmitted to the remote server (e.g., cloud) for analysis processing.

In general, the analysis may include the analysis of a baseline. A baseline ECG (e.g., a baseline heart vector) may be taken at the time the patient first subscribes and/or purchases the apparatus. The baseline signal may be vetted by the system. For example, the baseline signal may be examined to confirm that it is within some predefined 'normal' range of parameters. For example, the patent's baseline signal may be determined by doing a differential vector analysis of the baseline heart vector determined from the three orthogonal leads of the signal collection device. Multiple baseline measurements may be made and averaged, or the best one may be selected. Patients may be rejected as poor candidates where the baseline does not fall within expected parameters, e.g., because they have an irregular heart vector for some reason (including concurrent, undetected cardiac event). The system may periodically prompt the user to provide updated baseline signals.

In some variations the application software may provide quality control (QC) to check signals (e.g., a QC agent, a software agent, etc.), which may indicate that the baseline heart vector is sufficient or not; this may be done in real time, and may include both a signal quality check, which may be done at either or both the signal collection device and the mobile communications device (e.g., smartphone) and/or at the remote server. The QC agent may look for clarity of signal and/or may also confirm that the patient is not having heart attack. This may be part of a final level quality check The application software/firmware may also acquire risk factors from the patient. This may advantageously be done at the time of subscription. The patient may be prompted with a series of questions and/or may provide access to electronic medical records, indicating risk factors that are associated with a heart disorder (e.g., heart attack, etc.). Information may include patient-specific information (age, gender, weight, height, ethnicity, cholesterol level(s), blood pressure, etc.). The inquiry may be ordered and weighted. A minimum entry of risk factor information may be permitted (e.g., just age, just age and gender, etc.); if the minimum is not entered, the patient may not be permitted to subscribe.

As mentioned, the application may prompt the patient to update the baseline periodically (e.g., weekly, bimonthly, monthly, etc.) by sending messages (SMS/text messages) in the app or without the app (from the remote server).

In use, the patient may use the app to initiate an ECG recording either for testing (e.g., when experiencing symptoms associated with a cardiac event or otherwise feeling at risk for a cardiac event), or for updating the baseline, e.g., symptomatic or non-symptomatic. The user may initially indicate which type of recording is being made. If the patient indicates that they are experiencing symptoms, the app may expedite the ECG recording and analysis, to provide real-time response as quickly as possible. After the user starts the app and indicates from a user interface that they want a symptomatic ECG analysis to be made, the system may make the recording (and, using the QC agent, may take more than one recording) of the three orthogonal leads providing a heart vector. This recording may be initially examined, either locally or remotely (e.g., on the signal collection device, the smartphone/app and/or in the remote server), to determine if the immediate heart vector indicates that a cardiac event is likely occurring. If the likelihood is above a cutoff threshold based on the differential vector analysis of the heart vector (compared to the baseline heart vector) and in some variations in conjunction with the recorded patient-specific risk factors, then the patient may be immediately instructed, e.g., through the app or by contacting directly (e.g., phone, etc.) to seek medical attention. In some variations a medical professional may be directly contacted. If the preliminary analysis scores below the threshold, the patient may be prompted to provide additional symptom information, such as the location, duration, and/or intensity of the pain, the type of pain, sharpness of pain, etc. The symptom information may be collected with the app and transmitted to the remote server which may then combine this information with the patient risk factors and the differential heart vector information to generate a final score that may be sent to the patient and/or medial professional. If the score is above a threshold to indicate a likely cardiac event, the patient may be instructed to seek medical attention immediately and/or medical intervention may be contacted automatically. If the score is within an intermediate range, the patient may be instructed that they should follow-up with a medical provider. If the score is within the low likelihood range the patent may be informed of this as well. For intermediate or low scores, the patient may be instructed to do a follow-up reading within a predetermined amount of time (e.g., 10 minutes, 20 minutes, 30 minutes, etc.) which may be coordinated by the app.

Alternatively in some variations a report may be made to a physician that may then interpret the results manually or semi-manually, including the risk factors and symptoms, and may contact the patient directly, including through the app.

Figure 7:
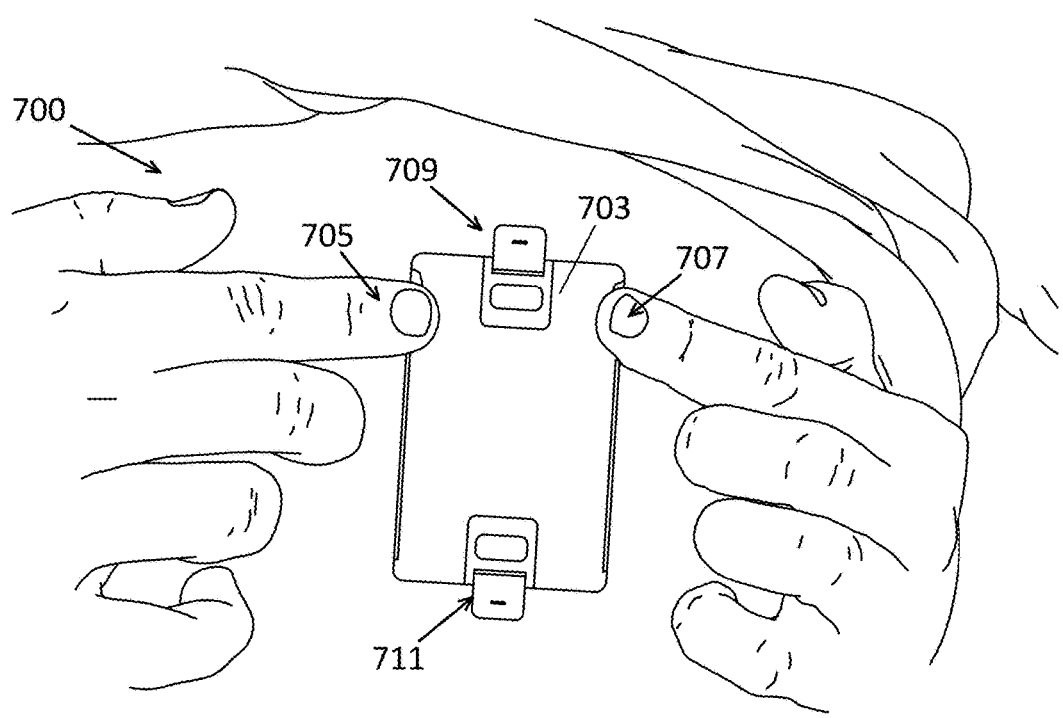
FIG. 7 is an example of a patient using the signal collection device as described herein.

FIG. 7 illustrates one example of a patient 700 that is holding a signal collection device 703 against their chest. The signal collection device includes a pair of extendable/pivoting chest electrodes 709, 711 that are separated by 10 cm or more when extended and in contact with the chest (vertically arranged, as shown). Two finger electrodes, one on the left 707 and one on the right 705 are used to complete the electrical contact and to hold the small, lightweight device to the chest, as shown. These contacts may allow three highly orthogonal leads to be determined (e.g., between the finger electrodes, between the chest electrodes and between a center point of a resistive network between the finger electrodes and one of the chest electrodes). The device may wirelessly communicate with a mobile communications device (e.g., smartphone) that may include an app (software or firmware) for confirming the signal quality and/or take additional recordings. The app may indicate by visual, audible, tactile or some combination of these that the recording has been made. The recording may be transmitted to the remote server, as shown schematically in FIG. 8.

Figure 8:
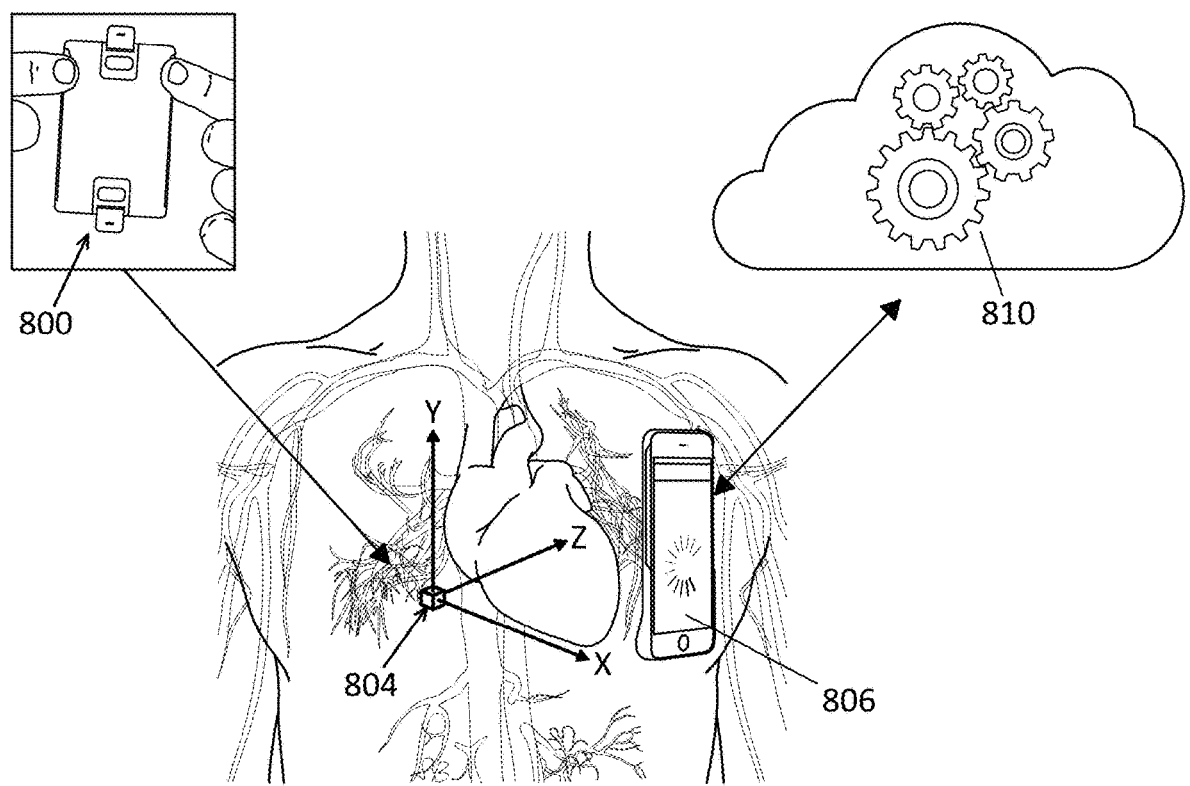
FIG. 8 schematically illustrates the operation of a system using a signal collection device.

FIG. 8 schematically illustrates an example of a system including a signal collection device 800 that may be used to determine the three orthogonal leads 804 accurately defining a heart vector; this signal may be transmitted to the patient's mobile telecommunications device 806 (e.g., phone, ipad, wearable electronics, etc.) which may process it and/or confirm the quality of the signal(s), store and/or transmit the signal to the remote server 810. The remote server may then communicate with the patient (e.g., back to the patient's mobile telecommunications device) or to a monitoring service and/or physician (not shown).

This methods and apparatuses described herein may be used with (and may improve upon) those described in U.S. patent application Ser. No. 15/096,159, titled "MOBILE THREE-LEAD CARDIAC MONITORING DEVICE AND METHOD FOR AUTOMATED DIAGNOSTICS", filed on Apr. 11, 2016, which claims priority to U.S. provisional patent application No. 62/145,431, titled "MOBILE THREE-LEAD CARDIAC MONITORING DEVICE AND METHOD FOR AUTOMATED DIAGNOSTICS" and filed on Apr. 9, 2015. These application are herein incorporated by reference in their entirety.

For example, the mobile three-lead cardiac monitoring device having a first compact and undeployed configuration and a second deployed configuration as described herein may be used for automatic remote diagnosis of heart conditions and may include automated diagnostic methods using these improved handheld cardiac apparatuses. These methods and apparatuses may implement a risk scoring model based on three risk components: pre-existing risk related to the patient's risk factors, chest pain risk related to current symptoms risk, and the recorded cardiac signals. Since these methods and apparatuses use risk factors and current symptoms as additional input, in addition to recording three orthogonal cardiac signals leads, not only AMI, but other cardiac conditions such as angina pectoris can be detected. In addition, using manually entered patient related data may provide for accurate setting of cardiac diagnosis, particularly in instances where an cardiac signals recording has low accuracy and precision, e.g., due to measurement interference. Thus, the methods and apparatuses described herein may improve the operation of current solutions by enabling not only automatic diagnostics of serious cardiac conditions but high accuracy diagnosis. The methods and apparatuses may be configured to include data acquisition, data processing (e.g., applying a scoring model) and sending diagnostic information to the patient about his heart conditions. The method may be performed on an apparatus configured as a handheld device that enables entering patient related data (e.g., pre-existing risk and current symptoms risk data), recording of cardiac signals by the patient and retrieving previously stored cardiac risk related data, in the situation where symptoms relate to an ongoing AMI or in similar situation. Any of these systems may include the mobile three-lead cardiac monitoring device having a first compact and undeployed configuration and a second deployed configuration as described herein. These systems may also include a user interface for entering patient's cardiac risk factors data and current symptoms data in textual form, as well as a memory for storing patient's cardiac risk factors data. Upon acquisition, the data may be transmitted to a remote processor. The processor may be configured to provide the patient with diagnostic information and transmit the diagnostic information back to the handheld device. The patient may decide, based on the received information, to take further actions, such as calling for emergency medical care. The handheld device may communicate the diagnostic information to the patient via characteristic sounds, voice messages or via a graphical display. The processor may be configured via hardware, software, firmware, or the like, and may process the signals may be received to produce a difference signal and extract information reliably related to detection of AMI.

For example, a mobile three-lead cardiac monitoring device having a first compact and undeployed configuration and a second deployed configuration as described herein may be configured to be operated by a patient when cardiac symptoms occur. The device may include a storage (e.g., memory) for storing data on patient's cardiac risk factors and other data, cardiac signals recording components (e.g., electrodes, circuitry, controller) for recording a patient's cardiac signals; the recording components may be similar to those disclosed in WO2016/164888A1, Bojovic et al, mentioned above. Patient related data (risk factors and current symptoms) may be entered and diagnostic message may be communicated to the patient, by equipping the device with a graphical user interface (e.g., touch screen or screen and a keyboard, etc.). The diagnostic information can also or alternatively be communicated to the patient via speaker through characteristic sounds or voice messages. The communication may occur via wired or wireless connection to a separate user-operated device, such as a smartphone or tablet, etc.

As mentioned the mobile three-lead cardiac monitoring device having a first compact and undeployed configuration and a second deployed configuration may be configured to record three substantially orthogonal cardiac signals leads, using the two chest electrodes and the two non-chest (finger) electrodes. In some electrode configurations, the device may have a ground electrode integrated anywhere at the surface of the device.

The mobile three-lead cardiac monitoring device having a first compact and undeployed configuration and a second deployed configuration as described herein may have various electrode configurations for recording three orthogonal cardiac lead signals. In one embodiment, the handheld device has two chest recording electrodes, one recording finger electrode on the left side of the device and one (or in some variations two) finger electrodes on the front side of the device, one recording and one ground electrode. The optimal position of the handheld device on the chest may be with center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum.

The four recording electrode configuration (e.g., having two chest and two finger electrodes) may fulfill the condition of high orthogonality, e.g., by recording signals in three main body directions: lateral (left arm-right arm), sagittal (back-front) and caudal (head-toes). For example, the signal in the lateral direction may be obtained by measuring the lead between left and right hand. The signal in the caudal direction may be obtained by measuring the lead between the two chest electrodes, with the condition that the distance between the chest electrodes in caudal direction is at least 5 cm, preferably greater than about 10 cm, in order to be greater than the approximate diameter of the heart muscle. In an ideal case, the signal in the sagittal direction would be measured between the back and the chest of the patient, which is not possible with the constraint of using only finger and chest electrodes. To overcome this, a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kOHM each, or unequal, the first one approximately 5 kOHM between the left-hand electrode and the CP, and the second one approximately 10 kOHM between the right hand electrode and the CP. This asymmetry reflects the left-side position of the heart in the torso, thus shifting the CP at the approximate electrical center of the heart. In this way, we obtain a three lead system that are substantially orthogonal.

Other similar lead configurations with the same CP may be chosen using the same set of two chest and two hand electrodes. Such a lead configuration may be substantially orthogonal, for example when both chest electrodes are used to record leads with the reference pole at the CP. Another possibility to define CP is using three electrodes, two hand electrodes and one chest electrode, and 3 resistors connected in a Y (star) configuration.

Other lead configurations without CP may also be used, like the configuration recording the signal of two chest electrodes and right-hand electrode with respect to left hand electrode. Such configurations without resistors or CP are more noise resistant to, for example, 50-60 Hz electrical noise, but have less orthogonal lead directions than the described ones using a CP. Generally, any other lead configuration using the same four described electrodes (a total of 20 configurations without a CP) results in leads that are non-coplanar and as such capture diagnostic signal in all three directions, but may lack a high degree of orthogonality. However, these configurations may have different levels of orthogonality, depending on the use of the right-hand electrode. The configuration using the right-hand electrode as the common reference pole in all 3 leads may have the lowest orthogonality, since the right-hand electrode is farthest from the heart among the four electrodes, and thus the angles between the vectors corresponding to the three leads are the smallest. However, this configuration with the lowest orthogonality is optimal for reconstruction of 12 leads ECG based on 3 lead signal, due to its small non-dipolar content. Nevertheless, the signals obtained using this configuration may be used with or without 12 leads reconstruction The effectiveness of the described solution is not affected if one or more chest electrodes are added on the back side of the device, and one or more corresponding additional leads are recorded and used in diagnostic algorithms. Also, the effectiveness will not be affected if front electrodes are pressed with palms or any other part of hands instead with the fingers.

For example, the apparatuses described herein may be used for remote diagnostics of cardiac conditions, such as acute myocardial infarction (AMI), atrial fibrillation (AFib), or the like. In particular, described herein are handheld devices with special electrode configurations capable of recording three orthogonal cardiac lead signals in an orientation-specific manner, and transmitting these signals to a processor (e.g., PC or other computing device). The processor may be configured to diagnose/detect AMI and transmit the diagnostic information back to the handheld device. The handheld device may communicate the diagnostic information to the patient via characteristic sounds, voice messages or via a graphical display. The processor may be configured via hardware, software, firmware, or the like, and may process the signals received to produce a difference signal and extract information reliably related to detection of AMI (and additional information of clinical relevance). Thus, these apparatuses and methods may perform automated detection of cardiac conditions on the basis of a 3-lead system, without the necessity for 12 L ECG reconstruction, reducing or eliminating the need for medical personnel to interpret the ECG, unlike prior art systems, which typically rely on medical personnel for such decisions. The automated diagnostic methods described herein, in combination with the improved handheld cardiac devices, address many of the needs and problems present in other systems.

Specifically, described herein are 3-lead cardiac recording devices for user placement on the chest, which include an arrangement of electrodes on both the front and back (or variations, on one or more sides, e.g., front-beveled sides) so that the devices may be held by both of the user's hand in a predefined orientation, so as to record a 3 lead cardiac signals when held against the user's chest. In order to fulfill above described functions, the handheld device may record three leads without using cables (e.g., may include only surface electrodes held or held against the body). Further, the resulting three leads are non-coplanar, and as close to orthogonal as possible. Finally, at least one electrode may be mounted on the front (and/or beveled sides) of the device, opposite to the chest side, to produce the force needed to hold device against the chest. There is no requirement for low, non-dipolar content, as the apparatuses and methods described herein do not require reconstruction of 12 L ECG from the measured 3 leads.

The mobile three-lead cardiac monitoring device having a first compact and undeployed configuration and a second deployed configuration devices described herein are configured to be mechanically stable and allow good electrical contact with the chest and to eliminate possibility for switching of finger contacts. The handheld device may be positioned on the chest with the center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum. A signal in the lateral direction may be obtained by measuring the lead between left and right hand. The signal in the caudal direction may be obtained by measuring the lead between the two chest electrodes, with the condition that the distance between the chest electrodes in caudal direction is at least 5 cm, preferably greater than about 10 cm, in order to be greater than the approximate diameter of the heart muscle. In an ideal case, the signal in the sagittal direction would be measured between the back and the chest of the patient, which is not possible with the constraint of using only finger and chest electrodes. To overcome this, we use a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kΩ each, or unequal, the first one approximately 5 kΩ between the left hand electrode and the CP, and the second one approximately 10 kΩ between the right hand electrode and the CP. This asymmetry reflects the left-side position of the heart in the torso, thus shifting the CP at the approximate electrical center of the heart. In this way we obtain a three lead system that are substantially orthogonal.

The mobile three-lead cardiac monitoring device having a first compact and undeployed configuration and a second deployed configuration as described herein may be configured as a stand-alone device incorporating an ECG recording module including amplifiers and AD convertor, data storage module, communication module operating on GSM, WWAN, or a similar telecommunication standard for communication with the remote processor (e.g., PC computer, pad, smartphone, etc.) and circuitry (e.g., Wi-Fi, Bluetooth, etc.) for communicating the diagnostic information to the user. Alternatively, it can be realized in conjunction with a mobile phone that.

The signal processing and diagnostic software can also be run on the processor (e.g., microprocessor) including a processor integrated in the handheld device, instead of running on a remote processor (e.g., PC computer). In this case, the communication of recorded information to the remote computer may no longer be required, except for data and processing backups. Also, when the diagnostic processing is carried out by a remote processor, a backup version of the software running on the microprocessor may be integrated in the handheld device, and may be used in situations when the user is in a zone without wireless network coverage.

Also described herein are methods and apparatuses for automated detection of AMI (or ischemia, the underlying physiological process) using the mobile three-lead cardiac monitoring device having a first compact and undeployed configuration and a second deployed configuration as described herein. These automated systems may include three cardiac leads that are substantially orthogonal contain the majority of diagnostic information that is present in the conventional 12-lead ECG. Each user may be registered in the diagnostic system by performing the first transmission of his/her non symptomatic cardiac recording with 3 cardiac leads. This first recording may be used as a reference baseline recording for AMI detection in the diagnostic recording (diagnostic recording meaning any further recording of the 3 cardiac leads of the same user). The availability of the reference baseline cardiac recording may allow distinguishing new from old ST segment elevation (STE) or equivalent parameter), and also other cardiac signal changes suggesting an AMI, providing a tool for automated AMI detection that may have diagnostic accuracy comparable to human ECG interpreters.

In one example, the user may place the device at a position that is different compared to the baseline position, which may compromise diagnostic accuracy. This misplacement is equivalent to a virtual change of the heart electrical axis in the 3D vector space defined by the 3 cardiac leads. In some variations, this angular change may be calculated for each test recording compared to baseline recording. If the angular change is greater than a threshold, such as 15 degrees, the user may be alerted to choose a position that is closer to the baseline position. If the change is lower than the threshold, it may be compensated for by rotating the signal loops of the test recording in the 3D vector space and get the signal that is substantially equivalent to the baseline signal.

The method for automated detection of AMI (or ischemia) may, in some variations, the following steps: placing the device in a recording position on the user chest; acquisition of a first 3 lead cardiac recording using the mobile three-lead cardiac monitoring device having a first compact and undeployed configuration and a second deployed configuration as described herein and communicating the signals to the processing unit; storage of the first recording in the data base of the processing unit as baseline recording for further comparison with any subsequent diagnostic recording; acquisition of the 3 lead cardiac diagnostic recording and communicating the signal to the processing unit, and processing of the resulting signals. Processing of the stored baseline signals and signals of the diagnostic recordings by the processing unit may include the following steps: preprocessing to eliminate power line interference, baseline wandering and muscle noise, obtain representative beat using fiducial points and median beat procedure, check for switching of the left and right finger, beat alignment to bring baseline and test recordings' representative beats in the same time frame so as the corresponding points are synchronized, compensation for chest electrode mispositioning in recording the test signal by compensating the heart electrical axis deviation in the 3 cardiac leads vector space, calculating difference signal, representing the change between baseline and diagnostic 3 cardiac leads signals, detection of cardiac signal changes suggesting ischemia by comparing the parameters of the test recording to the baseline recording or by comparing parameters on the difference signal to a predefined threshold, communicating information by the processing unit to the device, and finally communicating the diagnostic information by the device to the patient.

The STE is the most common ECG change in case of ischemia, usually measured at the J point or up to 80 msec later. Using STE as a parameter, the ischemic changes may be detected by comparing STE in the test recording to the baseline recording. Also, the ischemic changes may be detected by measuring the vector difference of the ST vector in the vector space defined by the 3 special cardiac leads (STVD), taking the baseline recording as a reference. As mentioned above, although these parameters (e.g., ST, J, STVD, STE), are defined with respect to traditional 12-lead ECG signals, they be herein refer to equivalent measures determined for the three cardiac leads (orthogonal signals) described herein. Thus, these equivalent points, regions or phenomena (e.g., STE, ST, J, STVD, etc.) may be identified by comparison between the cardiac signals described herein and traditional ECG signals, including traditional 12-lead ECG signals.

Other parameters of the cardiac signals may also be used for comparison with the baseline reference signal, such the "Clew", defined as the radius of the sphere which envelopes the vector signal hodograph between J and J+80 msec points.

Cardiac signals for an individual are highly repeatable as far as their shape is concerned. The changes of the signal shape are generally small for a healthy, or an individual in stable condition. For example, the change of the position of the heart with respect to rib cage can change the heart electrical axis by up to 10°. However, there are conditions when the signal shape may change over time, like STE caused by the Benign Early Repolarization (BER). Such signal changes are highly individual and could be significant. To compensate for such changes, a number of baseline recordings, taken by the user over a period of time, may be used to form a reference that forms a 3D contour in the vector space defined by the 3 special cardiac leads (instead of a single point when single baseline recording is used). In using such a 3D contour reference, the ST vector difference (STVD) may be defined as a distance from the 3D contour instead from the baseline ST vector. If more than one parameter is used for ischemia detection, such a reference contour may be constructed as a hyper-surface in a multidimensional parameter space defined by such parameters. In this case a hyper-distance from the reference hyper-surface will be defined in the said parameter space.

In some conditions, the signal shape changes may also be intermittent (the condition "comes and goes"), like in Brugada syndrome, WPW syndrome, Bundle Branch Blocks (BBB), etc. To compensate for signal changes in such conditions, two groups of baseline recordings (e.g., at least two recordings) may be used to define the reference, one with normal signals and one with the said intermittent condition present. These two groups will form two 3D contours in the vector space, forming a reference for comparison. These two 3D contours may overlap or not. If there is no overlap, the ST vector difference (STVD) will be defined as a distance from closest point on the two 3D contours. If more than one parameter is used for AMI/ ischemia detection, such reference contours would be constructed as two hyper-surfaces in a multidimensional parameter space defined by such parameters. In this case a hyper-distance from the reference hyper-surface will be defined in the said parameter space.

Primary use of the methods described herein may be applied to the detection of the most urgent cardiac diagnosis—the AMI. Additionally, the diagnostic methods (e.g., software) in the remote processor (or integrated processor in the handheld device) can detect other cardiac conditions such as chronic Coronary Arthery Disease (CAD), Left Ventricular Hypertrophy (LVH), Bundle Branch Blocks (BBB), Brugada syndrome, rhythm disorders such as Atrial Fibrillation (AF) etc.

Although the methods described herein do not require the reconstruction of conventional 12 lead ECG recordings, they may be used to reconstruct them. In many of the above mentioned conditions to be detected, treatment may be urgently needed, although to a lesser extent compared to AMI. Also, many of such conditions are transient, and may be detected using here described technology, but may not be present when the user later comes to the physician's office. In such a case, it would be useful to present the ECG signals for the condition that was discovered at the time of recording, so that physician may use it to confirm the diagnosis. Physicians are familiar with the conventional 12 lead ECG recording. Therefore, 3 special cardiac leads recorded when the condition was discovered may be transformed to produce an approximate reconstruction of conventional 12 lead ECG recording. Such reconstruction may be obtained by multiplication of the 3 special cardiac leads with a 12×3 matrix. This matrix may be obtained as a population matrix, that is a matrix with coefficients that are calculated as average, or median, values of individual matrices obtained by simultaneously recording conventional 12 lead ECG and 3 special cardiac leads in a population of individuals, with each individual matrix obtained using least squares method. The coefficients of such matrices are dependent of the shape of the user's body. Therefore, instead of using a single population matrix, multiple matrices may be used, each for a group of users defined by simple parameters of the body shape and structure, like gender, height, weight, chest circumference, etc., that may be easily obtained by the user. Also, matrix coefficients may be obtained as continuous functions of such body parameters.

Figure 9A:
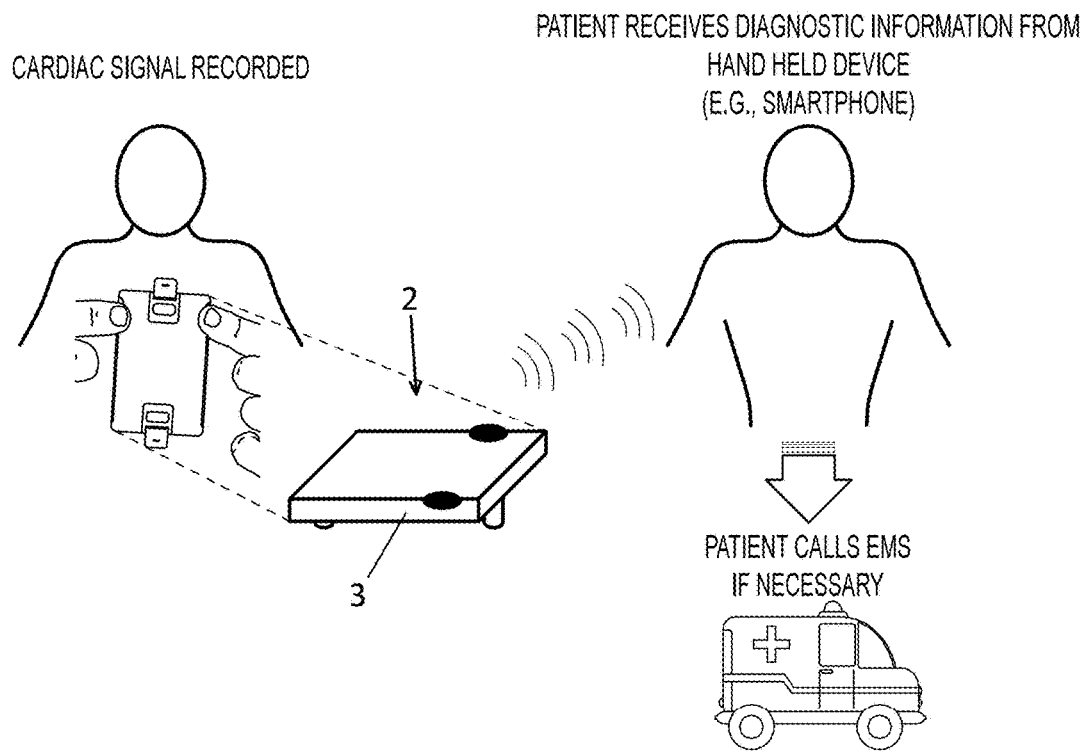
FIG. 9A shows one variation of a schematic configuration of a diagnostic system for detection of cardiac disorders such as AMI, including a mobile three-lead cardiac monitoring device having a first compact and undeployed configuration and a second deployed configuration as described herein.
Figure 9B:
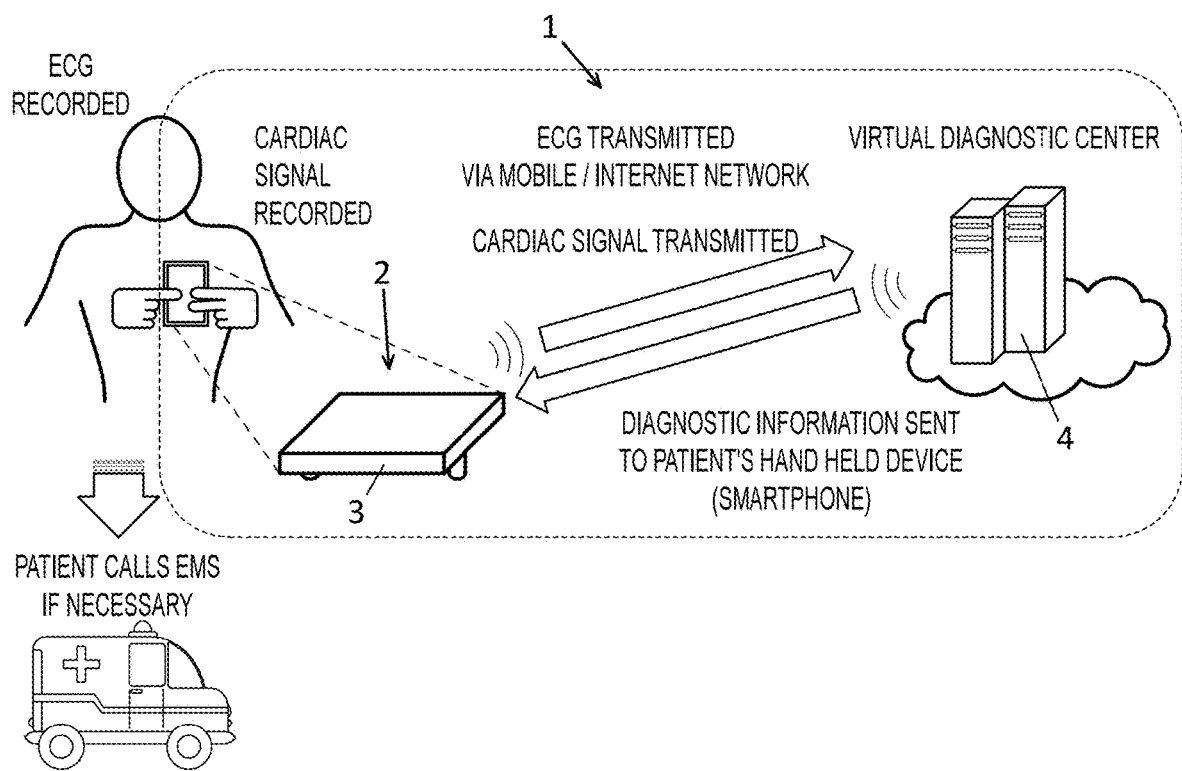
FIG. 9B is another schematic of a diagnostic system including a mobile three-lead cardiac monitoring device having a first compact and undeployed configuration and a second deployed configuration, wherein the processor is remote from the hand-held device.

FIG. 9A illustrates one variation of a method of operating a system for cardiac signal detection and/or diagnosis. In FIG. 9A, the user 2 may record cardiac signals (e.g., at two or more times), and the apparatus 3 (specifically, a mobile three-lead cardiac monitoring device having a first compact and undeployed configuration and a second deployed configuration as described herein) may process the three orthogonal leads to compare the different times (e.g., baseline vs. assay time). The processor of the apparatus 3 may further determine if the resulting differential signal indicates that cardiac problem, and can alert the user. The user (patient) can then get medical assistance as necessary. FIG. 9B shows a view of anther variations of a system and method for detecting cardiac dysfunction, including a system 1 for remote diagnostics of AMI including handheld device 2 incorporating built in electrodes for cardiac signal acquisition, mounted directly on the casing 3 of the hand held device and a PC computer 4 connected via a telecommunication link to the device.

The mobile three-lead cardiac monitoring device having a first compact and undeployed configuration and a second deployed configuration as described herein may further incorporate an cardiac signal recording circuitry including amplifiers and AD convertor for amplifying the signals detected by the electrodes, data storage (e.g., memory) for storing the recording signal, communication circuitry operating on GSM, WWAN, or a similar telecommunication standard for communication with the remote processor 4 and visual and/or audio (e.g., monitor, speaker, etc.) for communicating the diagnostic information to the user.

The mobile three-lead cardiac monitoring device having a first compact and undeployed configuration and a second deployed configuration as described herein may be communicating with the remote processor 4 via integrated communication circuitry. The remote processor 4 may communicate with the handheld device 2 via integrated communication module. The processor 4 may be equipped with diagnostic software for processing the received cardiac signals, producing diagnostic information and for transmitting the information back to the handheld device for communicating the diagnostic information to the patient via microphone producing characteristic sounds or voice messages or in the form of graphical information via a display integrated in the device. As a consequence, the system may be capable of performing automated detection of a cardiac condition on the basis of a 3-lead system and doesn't require interpretation of the processed diagnostic information by a specialist. Alternatively, instead of a remote processor, the system may include a microprocessor integrated in the casing 3 of the hand held device for processing the recorded cardiac signals and producing diagnostic information.

Figure 10:
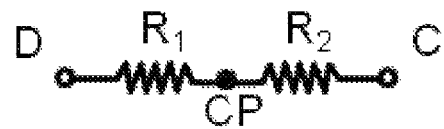
FIG. 10 shows a simple electrical scheme for obtaining a central point CP by connecting the electrodes of both hands via a simple resistive network with two resistors within a mobile three-lead cardiac monitoring device having a first compact and undeployed configuration and a second deployed configuration as described herein.

The example in FIG. 10 shows a simple electrical scheme for obtaining a central point CP by connecting the electrodes of both hands via a simple resistive network with two resistors.

Figure 11A:
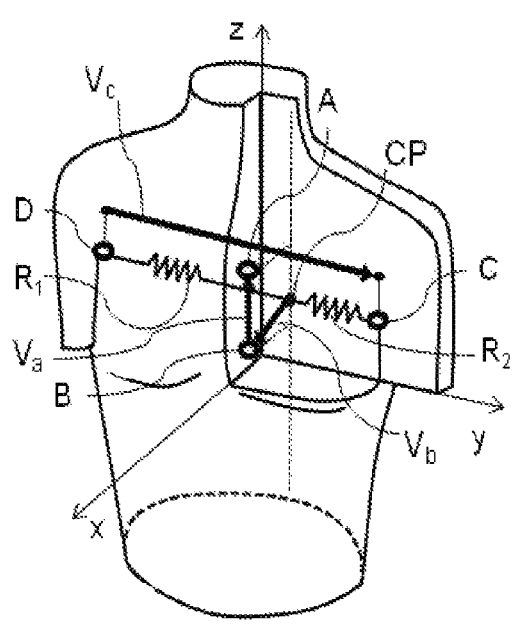
FIG. 11A shows schematic configuration of the three cardiac leads measured on the torso with one lead using central point as the reference pole.

FIG. 11A shows a spatial view of the lead configuration according to one embodiment, illustrating the arrangement of active electrodes A, B, C, D with respect to the body, as well as relative arrangement between the electrodes. FIG. 11B shows a simplified electrical scheme illustrating the same relative arrangement between the electrodes shown in FIG. 11A. For recording a lead in approximately sagittal direction, the voltage of the lower chest electrode B with respect to a central point CP may be obtained using the hand electrodes C, D and two resistors R1, R2. The two resistors R1, R2 can be equal, approximately 5 kΩ each, or unequal, approximately 5 kΩ between the left hand electrode and the CP, and 10 kΩ between the right hand electrode and the CP. This asymmetry may reflect the left-side position of the heart in the torso, thus putting the CP point at the approximate electrical center of the heart. In this way a substantially orthogonal three lead configuration may be obtained.

Figure 11C:
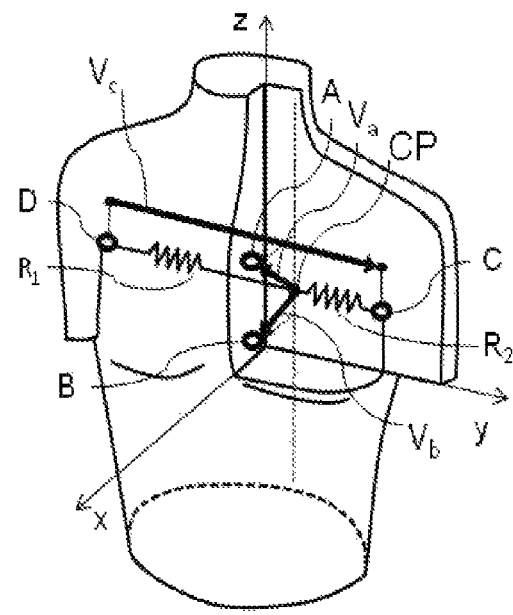
FIG. 11C shows a schematic configuration of the three cardiac leads measured on the torso with two leads using central point as the reference pole.
Figure 11B:
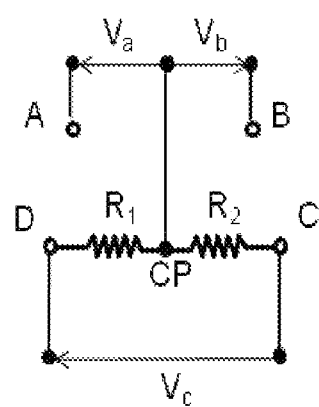
FIG. 11B shows an electrical circuit of the three cardiac leads with one lead using central point as the reference pole.
Figure 11D:
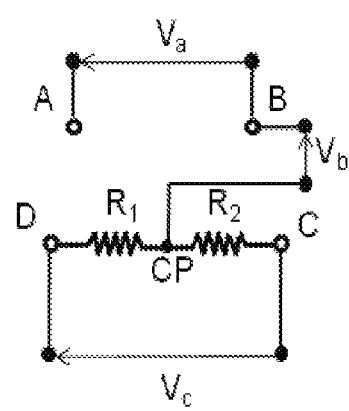
FIG. 11D is an electrical circuit of the three cardiac leads with two leads using central point as the reference pole.

FIG. 11C shows a spatial view of an alternative lead configuration with the central point CP using the same set of chest and hand electrodes A, B, C, D, illustrating arrangement of the electrodes with respect to the body, as well as relative arrangement between the electrodes. FIG. 11D shows simplified electrical scheme illustrating the same relative arrangement between the electrodes A, B, C, and D, shown in the FIG. 11C. This alternative lead configuration using a central point CP and measuring two leads between the CP and each of the chest electrodes is also substantially orthogonal, since the chest electrodes A, B are used to record leads with the reference pole at the CP which is obtained using two hand electrodes C, D and two resistors R1, R2.

Other lead configurations without central point CP and resistors may also be used, like the configuration shown in FIG. 11E, recording the signal of two chest electrodes and right hand electrode with respect to left hand electrode. Other two similar configurations are shown in FIGS. 11F and 11G. Such configurations without resistors are subject to less external interference, such as 50-60 Hz electrical noise, but have less orthogonal lead directions than the previously described ones using a CP. Generally, any other lead configuration using the same four described electrodes may result in non-coplanarity and, as such, captures the diagnostic signal in all three directions, but lacks high orthogonality. There are a total of 20 possible configurations without a CP, including ones shown in FIGS. 11E, 11F and 11G. However, these configurations have different levels of orthogonality, depending on the use of the right hand electrode. The configuration using the right hand electrode as the common reference pole in all 3 leads have the lowest orthogonality, since the right hand electrode is farthest from the heart among the four electrodes, and thus the angles between the vectors corresponding to the three leads are the smallest. The configurations using right hand electrode in two leads, such as the configuration shown in FIG. 11F, have better orthogonality, while best orthogonality is achieved in the configurations using right hand electrode in only one lead, such as the configurations shown in FIGS. 11E and 11G.

FIG. 12 shows a block diagram of the method for automated detection of AMI according to the preferred embodiment of a mobile three-lead cardiac monitoring device having a first compact and undeployed configuration and a second deployed configuration as described herein. A method for automated detection of AMI (or ischemia) may include all or some of the steps described below. First, placing the device in a recording position on the user chest.

An optimal position of the handheld device on the chest is with center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum. The user presses one active electrode and one ground electrodes with the fingers of the left hand and one active electrode with the finger of the right hand on the front side of the device.

The method may also include acquisition of a first 3 lead cardiac recording and communicating the signals to the processing unit. The user of the automated AMI diagnostic system may perform the recording of the 3-lead cardiac signal by holding the handheld device against the chest for a short period of time (e.g., at least 30 seconds, at least 20 seconds, at least 10 seconds, at least 5 seconds, etc.). The recording is stored in the memory of the device and then transmitted to the remote PC computer via commercial communication network.

The method may also include storage of the first recording in the data base of the processing unit as a baseline. After performing the first transmission of his/her cardiac signal, the cardiac signal recording is stored in a remote processor, and the user may be registered in the diagnostic system. Before this first transmission, the user or his/her MD/nurse may enter (via a dedicated web site) his medical data such as age, gender, risk factors for cardiovascular disease, etc., and indicate if he/she is currently having chest pain or any other symptom suggesting ischemia. If the answer is negative, this first cardiac recording is kept in the diagnostic system as a baseline recording that will serve as a reference for comparison in any further transmission when symptoms suggesting ischemia may occur.

The method may further include acquisition of the 3 lead cardiac diagnostic recording and communicating the signal to the processing unit. Any subsequent recording after the baseline recording has been accepted and stored in the data base is considered to be diagnostic recoding. The user of the automated AMI diagnostic system performs the diagnostic recording of the 3-lead cardiac signal by holding the handheld device against the chest for at least 10 seconds. The diagnostic recording is stored in the memory of the device and then transmitted to the remote PC computer via commercial communication network.

In general, the methods described herein may include processing of the stored signals of baseline and diagnostic recordings by the processing unit. Processing may include pre-processing. For example the apparatus/method may be configured to let Va,Vb,Vc be the 3 special leads recorded using the handheld device. Before performing any analysis, cardiac signal must be "cleaned" from the disturbing factors like power line interference, baseline wandering and muscle noise. While the former two may be removed using standard adaptive filtering and cubic spline techniques, respectively, the latter is suppressed using time-averaging median beat procedure.

To create a median beat, the entire cardiac signal may be delineated, resulting in set of fiducial points $S=\{P_1, P_2, \ldots, P_n\}$, where $Pi=\{Q_i, R_i, J_i, T_i, T_{i,end}\}$ (or points equivalent to these locations) are fiducial points of i-th beat. Based on S, the signal is then divided into n individual beats of the same length. Finally, individual beats are synchronized using cross-correlation (CC) and for each sample median value across all n beats is calculated. Thus, the entire cardiac signal is represented by the single most-representative median beat. A set of fiducial points $P=\{Q, R, J, T, T_{end}\}$ associated to the median beat are simply calculated as median values of the fiducial point of the individual beats.

Techniques for obtaining representative beat other than median beat may also be used. The delineation of the cardiac signal resulting in fiducial points for each beat may be done using different techniques like wavelet transform, support vector machine, etc.

The same pre-processing procedure is used for both baseline and diagnostic recording.

If the lead recorded between the left and the right hand, or other lead capturing the signal in the lateral direction, is inverted, the user is alerted to repeat the recording using the correct recording position.

The processing may also include beat alignment. For example, the apparatus or method may be configured to let B and D denote to the median beats extracted from the baseline and diagnostic cardiac signals, respectively, and PB and PD are their associated fiducial points. The goal of beat alignment is to bring B and D in the same time frame so as the corresponding points are accurately synchronized. This involves finding of such transformed B, referred to as B*, so that it is optimally synchronized to the D. The applied transformation is piece-wise uniform re-sampling of B, so that corresponding segments in B* and D, defined by PB and PD, respectively, have the same number of samples. Optimal alignment is obtained by searching for such fiducial points PB* that optimize cost function or similarity measure (SM) which quantifies the alignment:

$$P_B^* = \underset{P_B}{\mathrm{argopt}}\, SM \tag{1}$$

B* is then obtained by transforming B using the $P_B^*$.

In the present embodiment, we used CC which is commonly used SM for shape-based alignment problems. However, use of solely CC may lead to wrong alignment as shape in B and D may be significantly different. Therefore, we introduce weighting functions $f_{wi}$, which penalizes large deviations from the $P_B$, as the fiducial points $P_B$ are assumed to be accurately known:

$$f_{wi} = e^{-\left(\frac{\Delta P_{Bi}}{c_i}\right)^2} \tag{2}$$

where $i=Q, R, J, T, T_{end}$, $\Delta P_{Bi}$ is deviation from the i-th fiducial point and $c_i$ is scaling factor which depends on the fiducial points. Namely, as the R point is the most stable reference in cardiac signal, its deviation is penalized the most. On the other hand, as J and $T_{end}$ points are the least stable, thus, larger deviations are allowed. The overall SM is then calculated as product of CC and sum of weighting functions $f_{wi}$:

$$SM = CC(B(P_B), D)\Sigma_{i=1}^{5} f_{wi}(|P_B - P_{Bi}|) \tag{3}$$

Finally, according to the Eq. (1) the B* is obtained by finding optimum of SM given in Eq. (3).

The processing may also include compensation for chest electrode mispositioning. During regular use of the handheld device, chest electrodes may not be placed on the same spot every time, thus leading to changes in shape of cardiac signal even in absence of any pathology. This change can be modeled as "virtual" heart electrical axis deviation in the Va,Vb,Vc leads vector space if lead positions are assumed to be constant, with the heart electrical axis represented by the R vector—the heart vector at the moment of maximal magnitude in the QRS complex (or equivalent region in the three-lead cardiac signals described herein). However, this is undesired property as the difference signal ΔD will be significant, even though there are no pathologically induced changes. To overcome this problem, we transform D, resulting in D*=TD, so that its heart electrical axis overlaps with the axis of B*. The transform T is calculated using least squares method and Q-J segment (QRS complex) of D and B* as input.

In general, processing may also include calculating difference signal, representing the change between baseline and diagnostic cardiac leads signals. The difference signal ΔD* is calculated as:

$$\Delta D^* = D^* - B^* \tag{4}$$

Ultimately, such difference signal ΔD* will reflect solely pathologically induced changes and it will be independent on heart axis deviation.

Since the quality of the device misplacement compensation decreases with increase of the angle heart axis deviation, if the angular change is greater than a threshold, such as 15 deg, the user is prompted to choose a position that is closer to the baseline position.

The processing methods and apparatus described herein may also include detection of ischemic changes. The STE is the most common ECG change in case of ischemia, measured usually at the J point or up to 80 msec later. In the present solution, the ischemic changes are detected by comparing the test recording to the baseline recording. In the preferred embodiment, the parameter or "marker" for ischemia detection is STVM (or equivalent region in the cardiac signals described herein), the vector magnitude of the corrected difference signal $\Delta D^*$ at 80 msec after the J point (J+80 msec), compared to a predefined threshold, such as 0.1 mV.

In other embodiments, vector magnitude in other time points may be used as marker for ischemia, such as J point, J+60 msec, T max, etc. Other markers may be used that describe the shape of the ST segment (ECG signal segment between J and J+80 msec points, or similar). Such a marker is the "Clew", defined as the radius of the sphere which envelopes the vector signal hodograph between J and J+80 msec points. Also, other composite markers may be used, such as a logistic regression using a linear combination of STVM and Clew markers.

To compensate for signal shape change over time, a number of baseline recordings, taken by the user over a period of time, may be used to form a reference that forms a 3D contour in the vector space defined by the 3 special cardiac leads (instead of a single point when single baseline recording is used). In using such a 3D contour reference, the ST vector difference (STVD) will be defined as a distance from the 3D contour instead from the baseline ST vector. If more than one parameter is used for ischemia detection, such a reference contour would be constructed as a hyper-surface in a multidimensional parameter space defined by such parameters. In this case a hyper-distance from the reference hyper-surface will be defined in the said parameter space.

In users having cardiac condition with intermittent signal shape changes, compensation for such changes may be done by forming two groups of baseline recordings (at least two recordings) to define the reference, one with normal signals and one with the said condition. These two groups will form two 3D contours in the vector space, forming a reference for comparison, and the ST vector difference (STVD) will be defined as a distance from closest point on the two 3D contours. If more than one parameter is used for ischemia detection, such reference contours would be constructed as two hyper-surfaces in a multidimensional parameter space defined by such parameters. In this case a hyper-distance from the reference hyper-surface will be defined in the said parameter space.

Any of these methods and apparatuses may be configured for communicating information by the processing unit to the device. The created diagnostic information may be transmitted from the remote processor (e.g., a PC computer, server, etc.) to the device memory via commercial communication network. The method and apparatuses may also be configured for communicating the diagnostic information by the device to the patient. The received diagnostic information may be presented to the user in a form of characteristic sound, voice, graphics or text.

Additionally, an approximate conventional 12 lead ECG signal may be sent to the user's physician for evaluation. This signal may be produced as an approximate reconstruction of conventional 12 leads by transforming the 3 special cardiac leads signals recorded by the user. This reconstruction may be obtained by multiplication of the 3 special cardiac leads with a 12×3 matrix. In one embodiment, this matrix may be obtained computationally by using a general solution of potentials distribution on the surface of the human body, similar to those previously described for defining a conventional vector cardiogram. In another embodiment, this matrix may be obtained as a population matrix, that is a matrix with coefficients that are calculated as an average, or median, values of individual matrices obtained by simultaneously recording conventional 12 lead ECG and 3 special cardiac leads in a population of individuals, with each individual matrix obtained using least squares method. In yet another embodiment, multiple matrices may be used in corresponding user groups defined by simple parameters of the body shape and structure, like gender, height, weight, chest circumference, etc., that may be easily obtained by the user. Also, matrix coefficients may be obtained as continuous functions of such body parameters.

Device Positioning

The optimal placement of the mobile three-lead cardiac monitoring device having a first compact and undeployed configuration and a second deployed configuration as described herein may be on the chest is with center of the device on the left side of the chest approximately above the center of the heart muscle. In this position, the right edge of the device may be about 3 cm away from the midsternal line, the vertical middle line of the sternum, and the lower edge of the device is at about level of the lower end of the sternum. In an ideal case, the user chooses the optimal position on the chest in the first baseline recording and repeats this position in each future diagnostic recording. In such situation, the cardiac recordings are repeatable, and it is easy to detect cardiac signal changes suggesting an AMI.

Methods of Risk Assessment

A risk assessment model for evaluating patient's probability of having a serious condition such as Acute Myocardial Infarction (AMI) or cardiac ischemia is based on three types of input data: a) patient's risk factors, b) cardiac signals recording and c) current symptoms data.

The assessment method may comprise the following steps: 1) entering the risk factors data by patient himself and storing data in the system memory; 2) self-recording three lead ECG by the patient using hand-held device; 3) entering current symptoms data by the patient himself; 4) sending cardiac signals and current symptoms data to the remote processor/server; 5) processing data on the processor/server; 6) sending diagnostic message to the hand-held device; 7) communicating the diagnostic message to the patient using graphical or voice interface of the hand-held device. Step 1 is performed during the first use of the device/system by the patient. Steps 2-7 are performed when the patient is having symptoms or wants to do a cardiac check-up. The diagnostic message may refer to calling the emergency service, waiting for another measurement or ignoring the symptoms. In other words, the message has a form of instructions for the patient about what action actions to take.

In some embodiments, the automatic diagnostic system is based on cardiac risk evaluation using three risk components: cardiac signals risk (CSR), pre-existing risk (PER-patient's risk factors stored in the memory) and chest pain risk (CPR—current symptoms risk). Each risk is described with three risk levels: H-High, I-Intermediate, L-Low. The cardiac risk evaluation value is used to choose the diagnostic message communicated to the patient.

The final diagnostic message to the patient is given after up to 3 repeated diagnostic sessions 5-10 min apart. Each diagnostic session consists of cardiac signals recording and chest pain questionnaire (CPQ).

Cardiac Signals Risk (CSR):

Evaluation of cardiac signals risk may include three cardiac leads that are substantially orthogonal and contain the majority of diagnostic information that is present in the conventional 12-lead ECG. Each user may be registered in the diagnostic system by performing the first transmission of his/her non-symptomatic cardiac recording with 3 cardiac leads. This first recording may be used as a reference baseline recording for AMI detection in the diagnostic recording (diagnostic recording meaning any further recording of the 3 cardiac leads of the same user). The availability of the reference baseline cardiac recording may allow distinguishing new from old STE (ST segment elevation), and also other cardiac signal changes suggesting an AMI.

The STE is the most common ECG change in case of ischemia, measured usually at the J point or up to 80 msec later. In the present solution, the ischemic changes are detected by comparing the diagnostic recording to the baseline recording. In the preferred embodiment, the parameter or "marker" for ischemia detection is STVM, the vector magnitude of the difference signal ΔD* at 80 msec after the J point (J+80 msec), representing the change between baseline and diagnostic 3 cardiac leads vector. The difference signal ΔD* is calculated as (as discussed above, equation (4)):

$$\Delta D^* = D^* - B^*$$

Where D* is diagnostic 3 cardiac leads vector, and B* is baseline 3 cardiac leads vector.

In other embodiments, vector magnitude in other time points may be used as marker for ischemia, such as J point, J+60 msec, T max, etc. Other markers may be used that describe the shape of the ST segment (ECG signal segment between J and J+80 msec points, or similar). Such a marker is the "Clew", defined as the radius of the sphere which envelopes the vector signal between J and J+80 msec points. Also, other composite markers may be used, such as a logistic regression using a linear combination of STVM and Clew markers.

In some embodiments, automatic detection of cardiac signals signs of ischemia may be based solely on the diagnostic recording, without using the baseline recording. This approach may be used in case of a patient that is not the owner of the automatic device, and thus his baseline recording is not stored in the device's memory. In this case, the value of B* (baseline 3 cardiac leads vector) may be simply set to zero.

In some embodiments, automatic detection of cardiac signals signs of ischemia may be based on a conventional approach where the main signs of ischemia are ST segment shift and T wave inversion. These parameters or "markers" of ischemia are defined on conventional 12 lead ECG. The conventional 12 lead ECG may be synthesized from three orthogonal leads by using matrix transform, using an individual matrix or population baseline matrix.

The thresholds to classify CSR (H-High, I-Intermediate, L-Low) are defined as following: H—when CSR marker value is above the threshold (TH2). This threshold may correspond to the criterion for STEMI based on 12 lead ECG, such as 0.2 mV; I—when CSR marker value is between TH1 and TH2, where TH1 may be the optimal threshold for separation AMI vs. non-AMI signals, such as 0.1 mV; L—when CSR marker value is below TH1.

The threshold TH1 and TH2 may be determined from the previous experience and medical literature, or may be optimized using the cardiac signals recordings from a clinical data set.

Pre-Existing Risk (PER): (H-High, I-Intermediate, L-Low)

In some variations, the pre-existing risk (PER) evaluation algorithm is based on the 2013 ACC/AHA Guideline on the Assessment of Cardiovascular Risk. The variables that statistically merited inclusion in the risk assessment equations were age, total cholesterol, high-density lipoprotein cholesterol, systolic BP (including treated or untreated status), diabetes mellitus (diabetes), and current smoking status. Ten-year risks of atherosclerotic cardiovascular disease (ASCVD) events estimates are used for cutoffs between low (L for <5%), intermediate (I for 5-10%), and high (H for >10%) risk levels. For calculation the pre-existing risk (PER) variable, a "Pooled Cohort Equation" of exponential type is used:

$$PER = 1 - BaselineSurvivale^{(IndividualSum - MeanSum)} \quad (5)$$

The variable IndividualSum may be calculated as a linear combination of individual risk factors:

$$\begin{aligned}IndividualSum = &C1^*\ln(Age) + C3^*\ln(TotalCholesterol) + C4^*\ln(Age)^* \ln(TotalCholesterol) + C5^*\ln(HDL) + C6^*\ln(Age)^*\ln(HDL) + \\&C7^*TreatedSystolicBP^*\ln(SystolicBP) + \ln(HDL) + C9^*(1-TreatedSystolicBP)^*\ln(SystolicBP) + C11^*Smoker - C12^* \\&\ln(Age)^*Smoker + C13^*Diabetes\end{aligned}$$

Where coefficients C1-C13 and corresponding risk factor values may be used corresponding predetermined values (such as, but not limited to, those shown in Goff DC Jr, Lloyd-Jones D M, Bennett G, et al.: 2013 ACC/AHA guideline on the assessment of cardiovascular risk: a report of the American College of Cardiology/American Heart Association Task Force on Practice Guidelines. Circulation. 2014; 129 (suppl 2):S49-S73, herein incorporated by reference in its entirety. Alternative scores may be used for pre-existing risk (PER) evaluation Chest pain risk (CPR): (H-High, I-Intermediate, L-Low)

Chest pain risk (CPR—current symptoms risk) parameters are entered manually by the patients at the time the cardiac symptoms occur by means of a keyboard or touch screen. The chest pain risk parameters are chosen based on literature data and inventor's own clinical experience.

In the preferred embodiment, a list of nine parameters-questions may be used as shown in FIG. 13. Each answer to a question is assigned with a specific number of points, between −1 and 3, also shown in FIG. 13. The value of CPR variable is calculated as sum of points for all nine parameters-questions.

The CPR risk level is estimated with cutoffs between low (L for <2 points), intermediate (I for 2-5 points), and high (H for >5 points) risk levels.

In other embodiments, alternative questions/answers, number of points or cutoff values may be used.

Post-Test AMI Risk (PTR): (H-High, I-Intermediate, L-Low)

Post-test AMI risk (PTR) evaluation may be based on using three risk components: cardiac signals risk (CSR), pre-existing risk (PER) and chest pain risk (CPR) and can have three levels (H-High, I-Intermediate, L-Low). There are 27 possible combinations of CSR, PER and CPR values. The PTR value for each of these combinations is established based on literature data and inventor's own clinical experience. The values of all 27 possible combinations and corresponding PTR values are given at the FIG. 14.

Diagnostic Reports (Messages)

The diagnostic report is given to the patient after completing a diagnostic assessment that may have one, two or three diagnostic sessions (the cardiac signals recording and filling the chest pain questionnaire) performed by the patient in predefined time intervals, such as three sessions with 5-10 minutes time intervals.

The diagnostic report given to the patient may consist of different diagnostic messages suggesting the action that a patient should take. For example, the diagnostic message may suggest that the patient seeks medical help immediately, or Reassure regarding the benign nature of the symptoms. In the preferred embodiment, there are six possible messages: (1) the diagnostic system shows that you are having a heart attack. Call emergency service immediately. (2) The diagnostic system shows that probability of heart attack is high. You need to call emergency service and go the Emergency Room. (2A) You might be experiencing angina. Try to relax in quiet position, take a Nitro and repeat recording in 5 min. If the pain gets worse or lasts longer than your typical angina call emergency service. (3) Your chest pain episode might be a sign of a heart problem. You should notify your doctor and discuss whether further testing is necessary. If pain comes back call emergency service. (3A) The diagnostic system shows that you had an episode of angina. According to diagnostic system assessment the pain has resolved and ECG is back to normal. If this episode felt like your usual angina no urgent action is required. If the pattern of angina (severity, frequency, duration of pain) changes you need to notify your physician urgently. (4) Based on the diagnostic system assessment your chest pain is most likely not related to your heart. You should mention it to your doctor on your next appointment. Use your judgment to seek medical care if pain continues.

The messages 2A and 3A are used only for patients having angina pectoris as reported while filling their pre-existing risk (PER) questionnaire.

Diagnostic assessment by default has three sessions. The diagnostic assessment may be terminated with less than three sessions if conditions for termination the diagnostic assessment are satisfied.

In the preferred embodiment, the diagnostic message is chosen based on PTR (Post-test risk), CSR (cardiac signals risk), existence of chest pain, pre-existence of angina pectoris and the following set of rules:

Decision Rules

1. Score CSR=H in the 1st, 2nd or 3rd session terminates the diagnostic assessment and produces Message 1.

2. Scores PTR=H and CSR<H in the 1st, 2nd or 3rd session terminates the diagnostic assessment and produces Message 2.

3. Scores PTR<H sends request for additional session when the current number of completed sessions is less than 3.

4. After 3rd session, if PTR=I in any of the sessions and CP=1 (chest pain persists) in 3rd session, then Message 2 is produced.

5. After 3rd session, if PTR=I in any of the sessions and CP=0 (chest pain stopped) in 3rd session, then Message 3 is produced (only for non-angina patients).

6. After 3rd session, if PTR=L in all of three sessions and CP=0 (chest pain stopped) or CP=1 (chest pain persists) in 3rd session produces Message 4.

7. Patients with angina and scores PTR=H and CSR<H in the 1st or 2nd session produces Message 2A.

8. Patients with angina and score CSR=I or CSR=H in the 3rd session and CP=0 (chest pain stopped) produces Message 3.

9. Patients with angina and scores PTR=I or PTR=H in any of the 1st and 2nd sessions and CSR=L and CP=0 in the 3rd session produces Message 3A.

Figure 15:
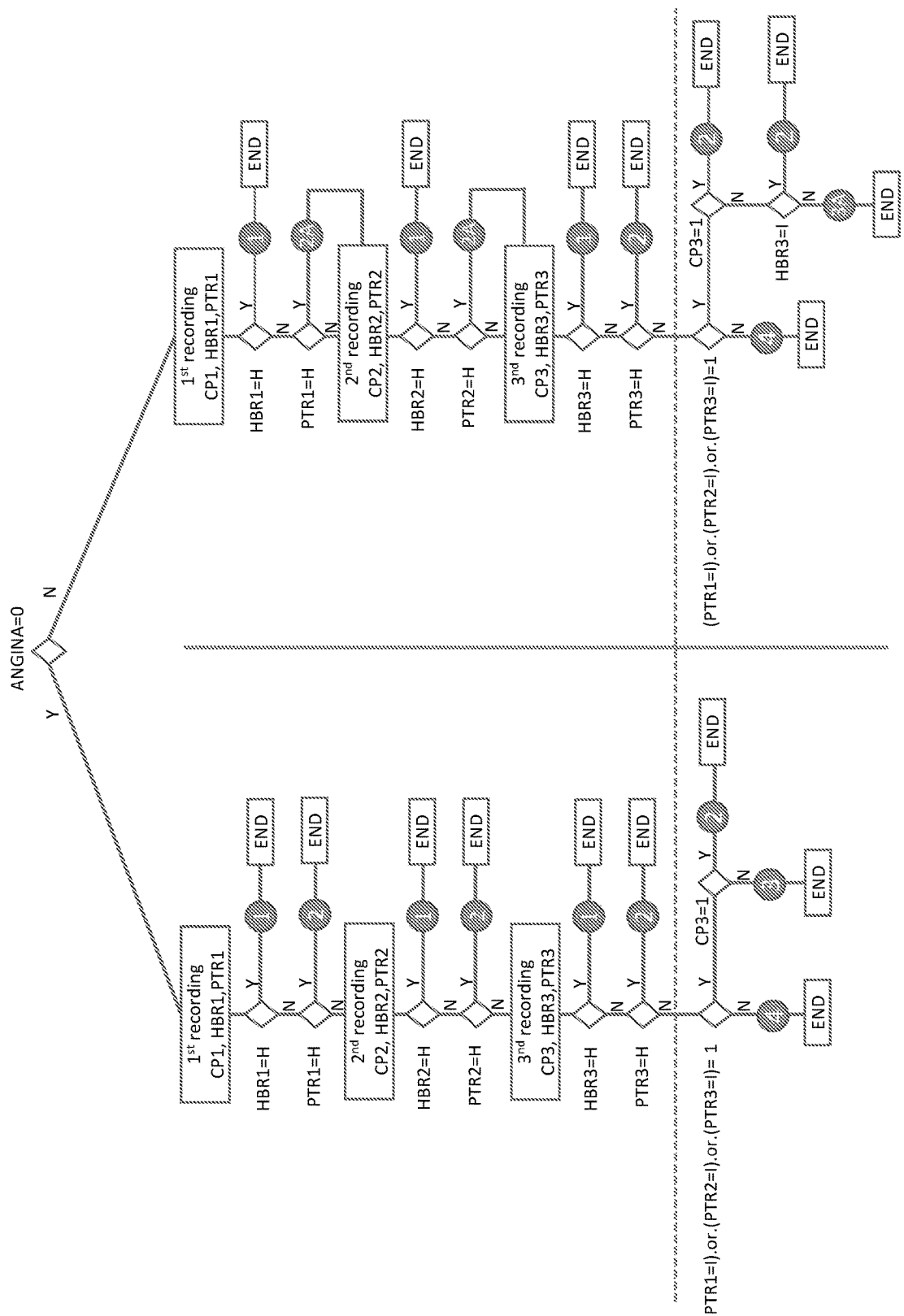
FIG. 15 is a process flow illustrating one method of indicating, to a patient, risk and treatment advice, as described herein.

FIG. 15 depicts the flowchart of the algorithm based on the above described rules 1-9. The flowchart has two branches for patients without and with angina. Each branch has three recording sessions with possible exits defined by rules 1-2 and assessment based on the completed three recording sessions according to the rules 3-9. After the any exit algorithm produces messages 1-4 (in the circles on the FIG. 15) related to AMI assessment or messages 2A and 3A (in the rectangles on the FIG. 15) related to the angina episodes.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A mobile three-lead cardiac monitoring device comprising:
   a casing having a front face and a rear face;
   two chest electrodes;
   two finger electrodes;
   two foldable arms pivotably attached to the casing on opposing ends thereof, wherein the two finger electrodes are disposed on the front face or edge of the casing and the two chest electrodes are disposed on the foldable arms; and
   two substantially prismatic compartments on either side of the casing, each configured for receiving the arms in a folded down position, each compartment having two lateral walls, a bottom, a front wall and a pin, wherein each pin connects two opposed lateral walls of each compartment.

2. The device according to claim 1, wherein each foldable arm has a recessed tapered portion at one end that accommodates one of the chest electrodes for acquiring signals from a patient's chest.

3. The device according to claim 1, wherein each arm comprises a torsion spring coaxial with the pin, said spring having a first and second tang, the first tang being engaged with the arm and the second tang being engaged with the casing.

4. The device according to claim 1, wherein the finger electrodes are disposed on chamfered portions of one or more longer edges of the front face, the chamfered portions being offset relative to a transverse centerline of the front face, and the arms being disposed adjacent to or at the shorter edges of the front face along a longitudinal centerline.

5. The device according to claim 1, further comprising a pair of compartments each having an opening adapted to receive a portion of one of the two foldable arms.

6. The device according to claim 1, wherein a length to thickness ratio of the casing is about 15 or greater and a length to width ratio is about 1.6 or greater.

7. The device according to claim 1, wherein a distance between the chest electrodes in an unfolded position is greater than about 10 cm.

8. The device according to claim 1, wherein an angle between the arms in the unfolded position is about 135 degrees.

9. A mobile three-lead cardiac monitoring device having a first compact and undeployed configuration and a second deployed configuration, the device comprising:
- a casing having a front face and a rear face;
- two chest electrodes;
- two finger electrodes;
- two foldable arms pivotably attached to the casing on opposing ends thereof, wherein the two finger electrodes are disposed on the front face or a front edge of the casing and the two chest electrodes are disposed on the foldable arms, wherein the foldable arms are folded flush with the rear face in the undeployed configuration and extend at an angle to the rear face in the deployed configuration; and
- a pair of compartments and one or more locks holding each of the arms within a compartment of the pair of compartments in a folded down position, wherein each arm has two spring plungers disposed in a cylinder perpendicular to lateral side of the arm, such that a tip of each plunger is configured to engage with a recesses formed in each lateral wall of the compartments.

10. The device according to claim 9, wherein each foldable arm has a recessed tapered portion at one end that accommodates one of the chest electrodes for acquiring signals from a patient's chest.

11. The device according to claim 9, wherein each arm comprises a torsion spring having a first and second tang, the first tang being engaged with the arm and the second tang being engaged with the casing.

12. The device according to claim 9, wherein the finger electrodes are disposed on chamfered portions of one or more longer edges of the front face.

13. The device according to claim 12, wherein the chamfered portions are offset relative to a transverse centerline of the front face, and the arms being disposed adjacent to or at the shorter edges of the front face along a longitudinal centerline.

14. The device according to claim 9, further comprising a pair of compartments each having an opening adapted to receive a portion of one of the two foldable arms.

15. The device according to claim 9, wherein a length to thickness ratio of the casing is about 15 or greater and a length to width ratio is about 1.6 or greater.

16. The device according to claim 9, wherein a distance between the chest electrodes in an unfolded position is greater than about 10 cm.

17. The device according to claim 9, wherein an angle between the arms in the unfolded position is about 135 degrees.

18. A mobile three-lead cardiac monitoring device comprising:
- a casing having a front face and a rear face;
- two chest electrodes;
- two finger electrodes;
- two foldable arms pivotably attached to the casing on opposing ends thereof, wherein the two finger electrodes are disposed on the front face or edge of the casing and the two chest electrodes are disposed on the foldable arms; and
- a pair of compartments and one or more locks holding each of the arms within a compartment of the pair of compartments in a folded down position, wherein each arm has two spring plungers disposed in a cylinder perpendicular to lateral side of the arm, such that a tip of each plunger is configured to engage with a recesses formed in each lateral wall of the compartments.

* * * * *